(12) United States Patent
Sharma et al.

(10) Patent No.: US 12,370,374 B2
(45) Date of Patent: Jul. 29, 2025

(54) METHODS OF AND APPARATUS FOR TREATMENT WITH FLASH RADIOTHERAPY

(71) Applicants: Varian Medical Systems, Inc.; Aarhus University, Aarhus (DK); Central Denmark Region, Viborg (DK)

(72) Inventors: Ricky Anupam Sharma, Palo Alto, CA (US); Sophia Pfister, Redwood City, CA (US); Marta Vilalta, Palo Alto, CA (US); Brita Singers Sørensen, Aarhus (DK); Per Rugaard Poulsen, Aarhus (DK); Gael Luis Boivin, Zurich (CH)

(73) Assignees: Varian Medical Systems, Inc., Palo Alto, CA (US); Aarhus University, Aarhus C (DK); Central Denmark Region, Viborg (DK)

( * ) Notice: Subject to any disclaimer, the term of this patent is extended or adjusted under 35 U.S.C. 154(b) by 381 days.

(21) Appl. No.: 17/968,392

(22) Filed: Oct. 18, 2022

(65) Prior Publication Data
US 2023/0141933 A1  May 11, 2023

Related U.S. Application Data

(60) Provisional application No. 63/257,211, filed on Oct. 19, 2021.

(51) Int. Cl.
*A61N 5/10* (2006.01)
(52) U.S. Cl.
CPC ........ *A61N 5/10* (2013.01); *A61N 2005/1087* (2013.01)

(58) Field of Classification Search
USPC ..................................... 250/492.1
See application file for complete search history.

(56) References Cited

U.S. PATENT DOCUMENTS 11,925,818 B2 * 3/2024 Michaud .............. A61N 5/1044
2016/0287905 A1 * 10/2016 Liger .................. A61N 5/1067
(Continued)

FOREIGN PATENT DOCUMENTS

WO   WO-2019166702 A1   9/2019

OTHER PUBLICATIONS

International Search Report and Written Opinion for International Application No. PCT/US2022/078290, mailed on Feb. 8, 2023, 14 pages.
(Continued)

*Primary Examiner* — Kiet T Nguyen
(74) *Attorney, Agent, or Firm* — COOLEY LLP

(57) ABSTRACT

The present disclosure relates to the field of radiotherapy, in particular, methods of and apparatus for treating cancer using ultra-high dose rate radiotherapy (FLASH). The apparatus may comprise a device configured to administer to the subject no more than five fractions of proton ultra-high dose rate radiotherapy (FLASH), said fractions having a range of radiation from 1.5 Gy to 60 Gy, collectively. The device may be configured such that the treatment is sufficient to prevent further growth of the tumor for at least 10% longer than standard of care radiotherapy, induce at least 10% more tumor regression than standard of care radiotherapy and/or delay tumor regrowth by at least about 2 months longer than standard of care radiotherapy.

23 Claims, 22 Drawing Sheets

(56) References Cited

U.S. PATENT DOCUMENTS

2019/0022411 A1    1/2019  Parry et al.
2021/0024564 A1*  1/2021  Rich ..................... A61K 45/06

OTHER PUBLICATIONS

Colangelo, N. et al., "The Importance and Clinical Implications of FLASH Ultra-High Dose-Rate Studies for Proton and Heavy Ion Radiotherapy," Radiat Res., Jan. 2020, 193(1):1-4.

Cunningham, S. et al., "FLASH Proton Pencil Beam Scanning Irradiation Minimizes Radiation-Induced Leg Contracture and Skin Toxicity in Mice," Cancers, Mar. 1, 2021, 13(1012):1-15.

Durante, M. et al., "Faster and safer? FLASH ultra-high dose rate in radiotherapy," Br J Radiol 2018, 91(20170628):1-4.

Liu, H. et al. "Proton therapy in clinical practice," Chin J Cancer., May 2011, 30(5):315-326.

Montay-Gruel, P. et al. "Hypo-fractionated FLASH-RT: An effective treatment against glioblastoma that significantly reduces neurocognitive side effects in mice," Clin. Cancer Res., Feb. 1, 2021, 27(3):775-784.

Sørensen, B. et al. "In vivo validation and tissue sparing factor for acute damage of pencil beam scanning proton FLASH," Radiotherapy and Oncology, 2022, 167:109-115.

Sørensen, B. et al. "Pencil beam scanning proton FLASH maintains tumor control while normal tissue damage is reduced in a mouse model," Radiotherapy and Oncology, 2022, 175:178-184.

Williams, M. et al. "Cognitive and behavioral effects of whole brain conventional or high dose rate (FLASH) proton irradiation in a neonatal Sprague Dawley rat model," PLoS ONE, 2022, 17(9):1-28.

Wilson, J. et al., Ultra-High Dose Rate (FLASH) Radiotherapy: Silver Bullet or Fool's Gold? Frontiers in Oncology, Jan. 17, 2020, 9(1563):1-12.

\* cited by examiner

Conv (1Gy/s)    FLASH (60Gy/s)    FLASH (115Gy/s)

METHODS OF AND APPARATUS FOR TREATMENT WITH FLASH RADIOTHERAPY

CROSS-REFERENCE TO RELATED APPLICATIONS

The present application claims the benefit of U.S. Provisional Patent Application No. 63/257,211, filed Oct. 19, 2021, which is incorporated herein by reference in its entirety.

FIELD

The present disclosure relates to the field of radiotherapy, in particular, methods of and apparatus for treating cancer using Ultra-High Dose Rate (FLASH) radiotherapy.

BACKGROUND

Radiotherapy is widely used for the treatment of cancer, with more than half of all cancer patients receiving x-ray radiation therapy. However, radiation-induced toxicity is common and often limits the dose of radiotherapy that can be delivered to a tumor (Cunningham et al., Cancers 2021, 13, 1012). In contrast to conventional x-ray radiation therapy, ultra-high dose rate (FLASH) radiotherapy has been suggested to be equally efficacious in controlling tumor growth while inducing less damage to healthy tissue, including skin and muscle (Cunningham 2021; Wilson et al., Front. Oncol. 2020 9:1563; Colangelo et al., Radiat Res. 2020 January; 193(1):1-4). Thus, FLASH radiotherapy has been suggested to widen the therapeutic window (Durante et al., *Br J Radiol* 2018; 91: 20170628).

The mechanisms which are responsible for the larger therapeutic window observed with FLASH are not fully understood, but several have been suggested, including, e.g., radiochemical depletion of oxygen and subsequent radioresistance conferred to the irradiated tissue with FLASH, and a modified immune response to FLASH due to irradiation of a greater proportion of circulating lymphocytes compared to total dose delivered in a single fraction (Wilson 2020).

The healthy tissue sparing of FLASH has mainly been investigated with electron beams. FLASH delivered with proton beams may have broader clinical perspectives for treatment in all tumor depths. FLASH dose rates can be obtained at clinical proton pencil beam scanning (PBS) facilities. However, the proton beam pattern differs markedly from electron beam FLASH.

Most available data so far are based to electron beams with limited utility for human treatments. Clinical proton therapy facilities can deliver FLASH dose rates at depths that provide access to all tumor sites. The preclinical data of proton FLASH are still very scarce.

In spite of promising in vivo results, the clinical potential of FLASH is not yet understood. The present disclosure provides a solution to this unmet need.

SUMMARY

In one aspect, provided herein is a method for treating cancer in a subject, the method comprising administering to the subject no more than five fractions of proton ultra-high dose rate radiotherapy (FLASH), said fractions having a range of radiation from 1.5 Gy to 60 Gy, collectively, wherein preferably the treatment is sufficient to prevent further growth of the tumor for at least 10% longer than standard of care radiotherapy.

In another aspect, provided herein is a method for treating cancer in a subject, the method comprising administering to the subject no more than five fractions of proton ultra-high dose rate radiotherapy (FLASH), said fractions having a range of radiation from 1.5 Gy to 60 Gy, collectively, wherein preferably the treatment is sufficient to induce at least 10% more tumor regression than standard of care radiotherapy.

In some embodiments, the dose of proton FLASH administered in accordance with a method described herein is equitoxic to the dose of conventional dose rate radiotherapy.

In another aspect, provided herein is a method for treating cancer in a subject, the method comprising administering to the subject no more than five fractions of proton ultra-high dose rate radiotherapy (FLASH), said fractions having a range of radiation from 1.5 Gy to 60 Gy, collectively, wherein preferably the treatment results in at least 10% less, at least 20% less, at least 30% less, at least 40% less, at least 50% less, at least 60% less, at least 70% less, at least 80% less, or more than 80% less healthy tissue toxicity than standard of care radiotherapy.

In some embodiments, the healthy tissue toxicity is skin toxicity. In some embodiments, the healthy tissue toxicity is muscle toxicity. In some embodiments, the healthy tissue toxicity is neurotoxicity.

In some embodiments, the collective dose of radiation delivered by proton FLASH radiotherapy in accordance with a method described herein is contraindicated in the subject. In some embodiments, the collective dose of radiation delivered by proton FLASH to the tumor is about 1.1 times, about 1.2 times, 1.5 times, about 2 times, about 3 times, about 4 times, about 5 times, about 10 times or about 15 times the dose of conventional dose rate radiotherapy indicated for the cancer. In some embodiments, the collective dose of radiation delivered to the tumor is about 10%, about 20%, about 30%, about 40%, about 50%, about 60%, about 70%, about 80%, about 90%, or about 100% higher than the dose of conventional dose rate radiotherapy indicated for the cancer.

In some embodiments, the cancer treated in accordance with a method described herein is a cancer for which radiotherapy is not indicated. In some embodiments, the cancer is lung cancer, head and neck cancer, brain cancer, breast cancer or skin cancer. In some embodiments, the subject is human.

In another aspect, provided herein is a method of treating brain cancer in a subject, the method comprising administering to the subject a total dose of about 8 Gy to about 60 Gy proton FLASH radiotherapy in seven fractions or less at a dose rate of 40 Gy/sec or higher.

In another aspect, provided herein is a method of treating head and neck cancer in a subject, the method comprising administering to the subject a total dose of about 8 Gy to about 60 Gy proton FLASH radiotherapy in seven fractions or less at a dose rate of 40 Gy/sec or higher.

In another aspect, provided herein is a method of treating breast cancer in a subject, the method comprising administering to the subject a total dose of about 8 Gy to about 60 Gy proton FLASH radiotherapy in seven fractions or less at a dose rate of 40 Gy/sec or higher.

In another aspect, there is provided apparatus as defined in the claims.

In another aspect, the invention relates to the use of no more than seven fractions of proton ultra-high dose rate radiotherapy (FLASH), said fractions having a range of radiation from 1.5 Gy to 60 Gy, collectively, in the treatment of cancer in a subject.

BRIEF DESCRIPTION OF THE DRAWINGS

FIG. 1A: Experimental setup for proton Proton Pencil Beam Scanning (PBS) of a mouse leg with FLASH and conventional dose rates (CONV). In vivo dosimetry was performed with alanine at the beam entrance and a scintillating ZnSe:O crystal placed right after the mouse leg target. FIG. 1B: Vertical dose profiles through the FLASH (grey) and CONV (black) field measured with radiochromic films at the entrance (left) and mouse leg depth (right).

FIG. 3A shows a representative comparison of normal foot (left) and a foot with radiation skin damage (right, score 2.5). FIGS. 3B-3F show dose response curves of five levels of acute damage to the skin at either CONV or FLASH dose rate. 154 mice are included in the CONV arm with 9-21 mice per dose point, and 138 mice in the FLASH arm with 7-11 mice per dose point. 95% Confidence intervals are indicated at $D_{50}$.

FIG. 4A shows a representative image of leg extension measurements with a 3D-printed jig at 84 days post IR. FIG. 4B shows leg contracture measured 3 weeks, 7 weeks and 12 weeks after treatment with CONV proton therapy or FLASH proton therapy. FIG. 4C shows skin toxicity score of CONV (square) and FLASH (triangle) mouse groups as function of time after irradiation. FIG. 4D shows decreased TGF-B1 level in the plasma 24 and 96 hours after FLASH versus CONV proton irradiation.

FIG. 6A shows equivalent percentage of mice achieved tumor control (complete disappearance of tumor within 3 months) after FLASH and CONV treatment. FIG. 6B shows the proportion of mice developing skin toxicity with FASH and CONV. FIG. 6C shows the proportion of mice developing fibrosis with FLASH and CONV. FIG. 6D shows a mouse leg bearing a subcutaneous C3H tumor.

FIG. 7A: The overall effect on latency where irradiated groups took longer to locate the platform compared with controls. FIG. 7B: The learning curves for latency. FIG. 7C: The overall effect on errors where irradiated groups had more errors to locate the platform. FIG. 7D: The learning curves for errors. N=19/sex/exposure except control male, 5-FLASH male, and 8-Conv females=18. *p<0.05, p<0.01, and *p<0.001 compared with controls.

FIG. 8A: The overall effect on latency where irradiated groups took longer to locate the platform compared with controls. FIG. 8B: The learning curves for latency. FIG. 8C: The overall effect on errors where irradiated groups had more errors to locate the platform. FIG. 8D: The learning curves for errors. N=19/sex/exposure except control male and 5-FLASH male=18. *p<0.05, p<0.01, and *p<0.001 compared with controls.

FIG. 8A shows equivalent survival when GL261 GBM tumor-bearing mice are treated with FLASH or CONV. FIG. 8B shows equivalent survival when PDGFRA-D842V-dnp53 GBM tumor-bearing mice are treated with FLASH or CONV. FIG. 8C shows survival proportions. FIG. 9D shows elative tumor growth of all 10 tumors per treatment plotted together (5 mice per treatment).

FIG. 11A shows an experimental schematic for Lewis lung carcinoma (LLC) orthotopic model of lung cancer, and timeline of irradiation and tissue harvest. FIG. 12B shows tumor volumes in mice treated with $FLASH^{pr}$ and $CONV^{pr}$ radiation. FIG. 12C shows representative images of tumor-bearing left lung lobe from each group at day 5 and day 8 post radiation. FIG. 12D shows representative images of H&E staining of lung tumors at day 5 and day 8 post treatment.

DETAILED DESCRIPTION

Figure 1A:
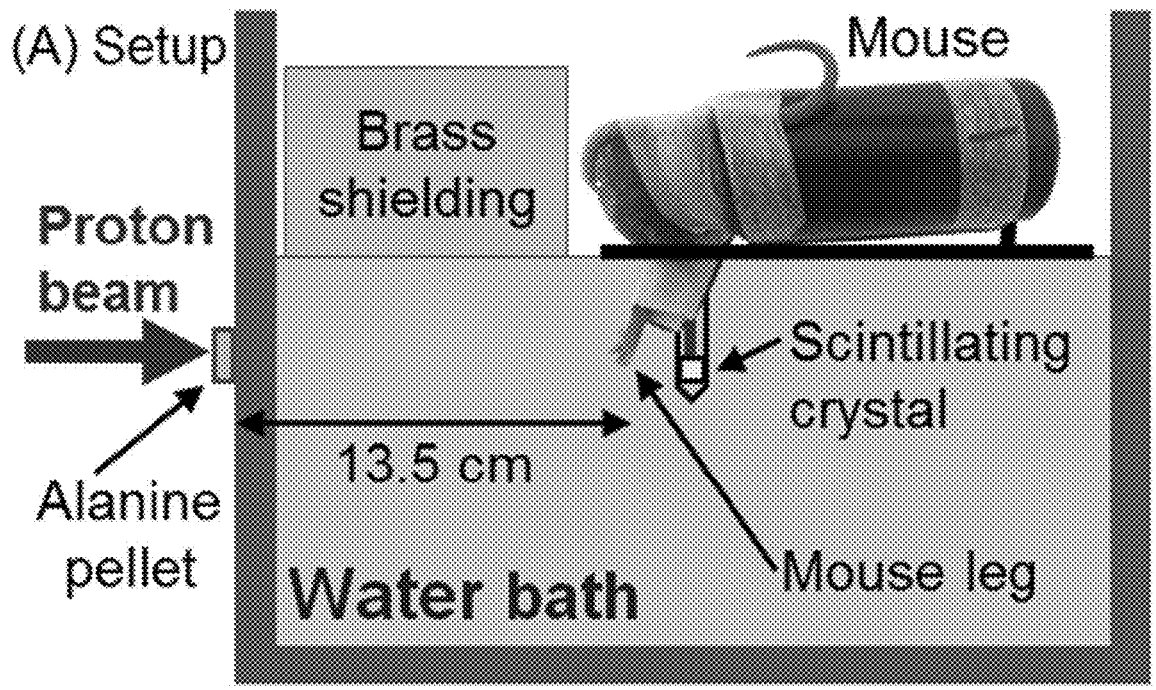
FIGS. 1A and 1B.

In one aspect, provided herein are methods of and apparatus for treating cancer in a subject comprising administering FLASH radiotherapy (e.g., proton FLASH radiotherapy) to the subject. In some embodiments, the administration of FLASH radiotherapy is better tolerated by the subject (e.g., results in less healthy tissue toxicity) than CONV therapy.

Radiotherapy

The FLASH radiotherapy of the methods described herein may be administered using any suitable system (or device) known in the art including, for example, an electron linear accelerator, a proton source, or an x-ray source. FLASH radiotherapy may be delivered using electrons delivered by a linear electron accelerator is described, for example, in Favaudon et al., Transl. Med. 6, 245ra93 (2014).

FLASH radiotherapy can be administered using, for example, high energy charged particles, electrons, protons, heavy ions, high energy photons, x-rays, gamma rays, or neutrons. In a preferred embodiment, the FLASH radiotherapy delivered in accordance with the methods described herein is proton FLASH radiotherapy.

Proton beam treatment has the advantage of being able to penetrate deeper into the tissue than electron beams. Furthermore, proton beams deposit the maximum of their energy at the end of their path, avoiding further penetration into healthy tissue (Liu, Chin J Cancer. 2011 May; 30(5): 315-326). FLASH proton radiotherapy may be administered using a passive beam scattering system (e.g., a single scattering system or double scattering system) or a dynamic spot scanning system. In some embodiments, the radiation therapy or treatment system used to deliver proton FLASH radiotherapy is a proton pencil beam scanning system.

Exemplary devices that may be used to administer FLASH radiation are described in, for example, U.S. Pat. No. 9,855,445, which is incorporated by reference herein in its entirety for the systems that may be used in the methods described herein. In some embodiments, the apparatus, device or system used to administer FLASH radiotherapy in accordance with a method described herein comprises a nozzle, an accelerator, and a beam transport system. The nozzle may further comprise a scanning magnet, which guides the beam towards the target, and a beam energy adjuster. The accelerator may be based on radio frequency (e.g., a linear accelerator, a cyclotron, or a synchrotron) or a laser-based accelerator.

The dose of radiotherapy (e.g., proton FLASH radiotherapy) that administered to a subject treated in accordance with a method described herein may depended on the characteristics of the subject and the cancer being treated. In some embodiments, the dose of FLASH radiotherapy (e.g., proton FLASH radiotherapy) administered is between 1 Gy and 60 Gy. In some embodiments, the dose of FLASH radiotherapy administered is about 1 Gy to about 5 Gy, about 5 Gy to about 10 Gy, about 10 Gy to about 15 Gy, about 15 Gy to about 20 Gy, about 20 Gy to about 25 Gy, about 25 Gy to about 30 Gy, about 30 Gy to about 35 Gy, about 35 Gy to about 40 Gy, about 40 Gy to about 45 Gy, about 45 Gy to about 50 Gy, about 50 Gy to about 55 Gy, about 55 Gy to about 60 Gy, about 60 Gy to about 65 Gy, or about 65 Gy to about 70 Gy. In some embodiments, the dose of FLASH radiotherapy (e.g., proton FLASH radiotherapy) administered in accordance with a method described herein is higher than a dose of radiation that would be indicated with conventional dose rate radiotherapy for the same disease.

In certain embodiments, the dose of FLASH radiotherapy (e.g., proton FLASH radiotherapy) administered in accordance with the methods described herein is an equitoxic dose to standard dose rate radiotherapy. The term "equitoxic dose" refers to a dose of FLASH radiotherapy (e.g., proton FLASH radiotherapy) that results in comparable levels of toxicity (e.g., no more than 10% increased or decreased) to a dose of conventional dose rate radiotherapy. In some embodiments, the dose of conventional dose rate therapy is a dose of radiation that may be administered as part of the standard of care treatment for a given tumor.

The dose of FLASH radiotherapy (e.g., proton FLASH radiotherapy) of the methods described herein may be substantially higher than the dose of conventional dose rate radiotherapy. In some embodiments, the collective dose of radiation delivered to the tumor using FLASH radiotherapy (e.g., proton FLASH radiotherapy) is about 1.1 times, about 1.2 times to about 2 times, about 2 times to about 3 times, about 3 times to about 4 times, about 4 times to about 5 times, about 5 times to about 6 times, about 6 times to about 7 times, about 7 times to about 8 times, about 8 times to about 9 times, about 9 times to about 10 times, about 10 times to about 15 times, about 15 times to about 20 times, about 20 times to about 25 times, or about 25 times to about 30 times the dose of conventional dose rate radiotherapy indicated for the cancer. In some embodiments, the collective dose of radiation delivered to the tumor using FLASH radiotherapy (e.g., proton FLASH radiotherapy) is about 1.2 times, about 2 times, about 3 times, about 4 times, about 5 times, about 10 times or about 15 times the dose of conventional dose rate radiotherapy indicated for the cancer. In some embodiments, the collective dose of radiation delivered to the tumor using FLASH radiotherapy (e.g., proton FLASH radiotherapy) is about 1.2 times to about 2 times, about 2 times to about 3 times, about 3 times to about 4 times, about 4 times to about 5 times, about 5 times to about 6 times, about 6 times to about 7 times, about 7 times to about 8 times, about 8 times to about 9 times, about 9 times to about 10 times, about 10 times to about 15 times, about 15 times to about 20 times, about 20 times to about 25 times, or about 25 times to about 30 times the dose of conventional dose rate radiotherapy that would be administered as the standard of care radiotherapy for the tumor. In some embodiments, the collective dose of radiation delivered to the tumor using FLASH radiotherapy (e.g., proton FLASH radiotherapy) is about 1.2 times, about 1.5 times, about 2 times, about 3 times, about 4 times, about 5 times, about 10 times or about 15 times the dose of conventional dose rate radiotherapy that would be administered as the standard of care radiotherapy for the tumor. One of skill in the art will appreciate that a standard of care regimen for a cancer may comprise not just radiotherapy but also chemotherapy or other interventions. As used herein, the term "standard of care radiotherapy" refers to only the radiotherapy component of a standard of care regimen for a given cancer. The additional components (e.g., chemotherapy) may remain unchanged or may require adjustments. In some embodiments, the standard of care radiotherapy is the treatment set out in the ASTRO Clinical Practice Guidelines (available at www.astro.org/Patient-Care-and-Research/Clinical-Practice-Statements/Clinical-Practice-Guidelines).

In some embodiments, the collective dose of radiation delivered to the tumor using FLASH radiotherapy (e.g., proton FLASH radiotherapy) is about 5% to 10%, about 10% to about 15%, about 15% to about 20%, about 20% to about 25%, about 25% to about 30%, about 30% to about 40%, about 40% to about 50%, about 50% to about 60%, about 60% to about 70%, about 70% to about 80%, about 80% to about 90%, or about 90% to about 100% higher than the dose of conventional dose rate radiotherapy indicated for the cancer. In some embodiments, the collective dose of radiation delivered to the tumor using FLASH radiotherapy (e.g., proton FLASH radiotherapy) is about 10%, about 20%, about 30%, about 40%, about 50%, about 60%, about 70%, about 80%, about 90%, or about 100% higher than the dose of conventional dose rate radiotherapy indicated for the cancer. In some embodiments, the collective dose of radiation delivered to the tumor using FLASH radiotherapy (e.g., proton FLASH radiotherapy) is about 5% to 10%, about 10% to about 15%, about 15% to about 20%, about 20% to about 25%, about 25% to about 30%, about 30% to about 40%, about 40% to about 50%, about 50% to about 60%, about 60% to about 70%, about 70% to about 80%, about 80% to about 90%, or about 90% to about 100% higher than the dose of conventional dose rate radiotherapy indicated for the cancer. In some embodiments, the collective dose of radiation delivered to the tumor using FLASH radiotherapy (e.g., proton FLASH radiotherapy) is about 10%, about 20%, about 30%, about 40%, about 50%, about 60%, about 70%, about 80%, about 90%, or about 100% higher than the dose of conventional dose rate that would be administered as the standard of care radiotherapy for the tumor.

As used herein, the term "conventional dose rate radiotherapy" is used to refer to radiotherapy that is administered at rates of about 1 Gy/sec or less. One of skill in the art will appreciate that the radiation dose of conventional dose rate therapy that is administered will depend on many variables, including, without limitation, the tumor being treated, the stage and/or progression of the disease, patient co-morbidities, concurrent treatments, the device used to administer the radiation, and prior therapies. Thus, when referring to a dose of FLASH radiotherapy (e.g., proton FLASH radiotherapy) being "higher than the dose of conventional dose rate radiotherapy indicated for the cancer," it is to be understood that the precise dose of conventional dose rate radiotherapy depends on these variables. Generally, conventional dose rate radiotherapy is administered at a rate of 1 Gy/sec or less.

The FLASH radiotherapy (e.g., proton FLASH radiotherapy) of a method described herein may be delivered in a pulsed manner, a continuous manner, or a quasi-continuous manner. In some embodiments, the FLASH radiotherapy (e.g., proton FLASH radiotherapy) is administered in a pulsed manner with pulses at a frequency of about 100 Hz. In some embodiments, the dose of FLASH radiotherapy (e.g., proton FLASH radiotherapy) is delivered in a single pulse. In some embodiments, the dose of FLASH radiotherapy (e.g., proton FLASH radiotherapy) is delivered in a series of two or more pulses. Each pulse can have a duration of less than a second, several seconds, or several minutes. The interval between pulses may also last less than a second, several seconds, or several minutes. In some embodiments, each pulse in a series of pulses has the same duration. In some embodiments, the pulses in a series of pulses have different durations. In some embodiments, the intervals between each pulse in a series of pulses have the same duration. In some embodiments, the intervals between pulses in a series of pulses have different durations.

The dose and pulse parameters may be varied by a person skilled in the art to optimize the therapeutic effect. In some embodiments, the dose per pulse is at least 1 Gy, at least 2 Gy, at least 3 Gy, at least 4 Gy, or at least 5 Gy.

FLASH radiotherapy (e.g., proton FLASH radiotherapy) is administered at substantially higher dose rates than conventional dose rate therapy. Thus, in some embodiments, a dose of FLASH radiotherapy is administered at a rate of at least 40 Gy/sec, at least 50 Gy/sec, at least 60 Gy/sec, at least 70 Gy/sec, at least 80 Gy/sec, at least 90 Gy/sec, at least 100 Gy/sec, at least 110 Gy/sec, at least 120 Gy/sec, at least 130 Gy/sec, at least 140 Gy/sec, at least 150 Gy/sec, at least 160 Gy/sec, at least 170 Gy/sec, at least 180 Gy/sec, at least 190 Gy/sec, at least 200 Gy/sec, 210 Gy/sec, at least 220 Gy/sec, at least 230 Gy/sec, at least 240 Gy/sec, or at least 250 Gy/sec is administered.

In some embodiments, a dose of FLASH radiotherapy (e.g., proton FLASH radiotherapy) is administered at a rate of about 40 Gy/sec to about 75 Gy/sec, about 75 Gy/sec to about 100 Gy/sec, about 100 Gy/sec, to about 150 Gy/sec, about 150 Gy/sec to about 200 Gy/sec, about 200 Gy/sec to about 250 Gy/sec, about 250 Gy/sec to about 300 Gy/sec, about 300 Gy/sec to about 350 Gy/sec, or about 350 Gy/sec to about 400 Gy/sec is administered.

In some embodiments, a dose of FLASH radiotherapy (e.g., proton FLASH radiotherapy) is administered at a rate of about 40 Gy/sec, about 50 Gy/sec, about 60 Gy/sec, about 70 Gy/sec, about 80 Gy/sec, about 90 Gy/sec, about 100 Gy/sec, about 110 Gy/sec, about 120 Gy/sec, about 130 Gy/sec, about 140 Gy/sec, about 150 Gy/sec, about 160 Gy/sec, about 170 Gy/sec, about 180 Gy/sec, about 190 Gy/sec, about 200 Gy/sec, about 210 Gy/sec, about 220 Gy/sec, about 230 Gy/sec, about 240 Gy/sec, about 250 Gy/sec, about 260 Gy/sec, about 270 Gy/sec, about 280 Gy/sec, about 290 Gy/sec, or about 300 Gy/sec is administered.

In some embodiments, the dose of FLASH radiotherapy (e.g., proton FLASH radiotherapy) is administered as fractionated doses, i.e., in a series of small doses over a period of time. Dose fractionation is used with conventional radiotherapy to reduce the incidence of radiation-induced side effects (Colangelo 2020). Generally, a dose of conventional radiotherapy is fractionated into daily doses administered over weeks in order to achieve an acceptable therapeutic index (Dutt et al., *Semin Radiat Oncol.* 2020 Apr. 30(2): 194-200). Commonly, radiotherapy for solid tumors (e.g., standard of care radiotherapy) is fractionated into small doses of 1.8-2 Gy per day, delivered 5 days per week over the course of 6 to 8 weeks, resulting in a total doses of 60-80 Gy (Dutt et al., 2020)). Fractions of radiation may also be administered twice a day (at least 6 hours apart). Accelerated radiotherapy uses smaller fractions of, for example, about 1.5 Gy. Hypofractionated radiotherapy may be used when the anatomy allows and is generally administered as a treatment composed of 1 to 7 fractions, with each dose ranging from 24 to 7 Gy.

In some embodiments, no more than five fractions of FLASH radiotherapy (e.g., proton FLASH radiotherapy) are administered. In some embodiments, no more than six fractions of FLASH radiotherapy (e.g., proton FLASH radiotherapy) are administered. In some embodiments, no more than seven fractions of FLASH radiotherapy (e.g., proton FLASH radiotherapy) are administered.

In some embodiments, the dose of FLASH radiotherapy is administered as 7 fractions of 5 Gy each. In some embodiments, the dose of FLASH radiotherapy is administered as 7 fractions of 6 Gy each. In some embodiments, the dose of FLASH radiotherapy is administered as 7 fractions of 7 Gy each.

The administration of a given dose of radiotherapy in fewer fractions decreases the burden on patients and physicians, since fewer visits are necessary for the patient to receive the full dose of radiation. In some embodiments, two fractions of FLASH radiotherapy (e.g., proton FLASH radiotherapy) are administered. In some embodiments, three fractions of FLASH radiotherapy (e.g., proton FLASH radiotherapy) are administered. In some embodiments, four fractions of FLASH radiotherapy (e.g., proton FLASH radiotherapy) are administered. In some embodiments, five fractions of FLASH radiotherapy (e.g., proton FLASH radiotherapy) are administered. Without wishing to be bound by theory, it is believed that FLASH radiotherapy (e.g., proton FLASH radiotherapy) can be delivered in fewer fractions than the same dose could be delivered by conventional radiotherapy due to the tissue sparing effect of FLASH radiotherapy (e.g., proton FLASH radiotherapy).

A dose may be administered in one or more fields. The field is the part of the tumor being irradiated by a specific beam. Thus, multiple beams may be used to deliver a desired dose of FLASH radiotherapy (e.g., proton FLASH radiotherapy).

Radiotherapy is delivered to fields, i.e., areas of the body of the subject that is being treated. Without wishing to be bound by theory, it is believed that larger fields can be irradiated with FLASH radiotherapy (e.g., proton FLASH radiotherapy) than with conventional radiotherapy due to the issue sparing effect of FLASH radiotherapy. Thus, in some embodiments of a method provided herein, the field treated with FLASH radiotherapy (e.g., proton FLASH radiotherapy) is larger (e.g., about 10%, about 20%, about 30%, about 40%, about 50%, about 60%, about 70%, about 80%, about 90%, or more than 90% larger) than the field treated with conventional dose rate radiotherapy (e.g., standard of care radiotherapy). In some embodiments, the field is the entire brain. In some embodiments, the field is the entire breast. In some embodiments, the field is the entire pelvis. In some embodiments, the field is the entire thorax. In some embodiments, the field is the entire hemithorax.

In some embodiments, the cancer treated in accordance with the methods described herein is thoracic cancer (e.g., lung cancer), head and neck cancer, brain cancer (e.g., glioblastoma), skin cancer, prostate cancer, pelvic cancer or liver cancer. In some embodiments, the cancer is a cancer for which conventional dose rate radiotherapy (e.g., standard of care radiotherapy) is not indicated.

As used herein, the terms "patient" and "subject" are used interchangeably. In certain embodiments, the subject is human. In some embodiments, the subject is a human adult. In some embodiments, the subject is a human child. In some embodiments, the patient has undergone prior therapy for cancer, e.g., prior radiotherapy, prior chemotherapy, or a combination thereof. In some embodiments, the patient's cancer has recurred after the prior therapy (e.g., after prior radiotherapy, prior chemotherapy, or a combination thereof). In some embodiments, a patient's cancer has recurred after ablative radiotherapy.

Healthy Tissue Toxicity

In some embodiments, the administration of FLASH radiotherapy (e.g., proton FLASH radiotherapy) according to a method described herein results in less healthy tissue toxicity than conventional dose rate radiotherapy. Conventional dose rate radiotherapy may be, for example, radiation therapy with conventional x-ray radiation at a rate of 2 Gy/sec or less, e.g., a daily dose of 1.8-2 Gy radiation for 6-7 weeks. In some embodiments, the healthy tissue toxicity of a method of treatment described herein is decreased by about 5% to about 10%, by about 10% to about 20%, by about 20% to about 30%, by about 30% to about 40%, by about 40% to about 50%, by about 50% to about 60%, by about 60% to about 70%, by about 70% to about 80%, by about 80% to about 90%, or by more than about 90% compared to conventional dose rate radiotherapy (e.g., standard of care radiotherapy) as determined by a method known in the art or described herein (e.g., determined using a biomarker described herein).

The radiation tolerance of a tissue depends on several factors, including, for example, the organ being treated, age, comorbidities, prior treatment, fractionation of the dose, duration of treatment, etc. Radiation-induced toxicity in normal tissue can appear acutely or be delayed by weeks or months after the treatment. The signs and symptoms may vary, depending on the site or organ. Estimates of the total doses of radiation that can be sustained by healthy tissues have been described in the art. See, e.g., Emami, *Reports of Radiotherapy and Oncology;* 2013, 1(1):35-48 and Emami et al., *Int J. Radiation Oncology Biol. Phys.* Vol. 21, pp. 109-122, each of which is incorporated herein by reference in its entirety for examples of normal tissue tolerance to radiotherapy.

The healthy tissue toxicity of a method described herein may be determined using any suitable method known in the art or described herein. In some embodiments, the healthy tissue toxicity is skin toxicity, e.g., necrosis or moist desquamation. In some embodiments, the healthy tissue toxicity is neurotoxicity, e.g., cognition or neuroinflammation. In some embodiments, the healthy tissue toxicity is brain toxicity. In some embodiments, the healthy tissue toxicity is lung toxicity, e.g., inflammation or fibrosis. In some embodiment, the healthy tissue toxicity is gastrointestinal toxicity, e.g., intestinal crypt ablation or GI syndrome). In some embodiments, the healthy tissue toxicity is muscle toxicity. In some embodiments, the healthy tissue toxicity is determined using a biomarker.

Any suitable biomarker known in the art or described herein may be used to determine the healthy tissue toxicity of a method of treatment described herein. In some embodiments, the biomarker is a biomarker of genotoxicity (e.g., stable translocations, telomere length, histone H2AX phosphorylation, dicentric chromosome aberrations, or micronuclei). In some embodiments, the biomarker is a biomarker of brain toxicity (e.g., circulating levels of FGF2, VEGF, IL-1, and/or cortisol, and/or levels of 14-3-3 beta protein in the cerebral spinal fluid). In some embodiments, the biomarker is a biomarker of lung toxicity (e.g., TGFα, TGFβ1, IL-1, IL-6, IL-8, KL-6, PDGF, and/or TNFα expression, and/or expression of pulmonary surfactant apoproteins). In some embodiments, the biomarker is a metabolic biomarker (e.g., oxidized lipid product involved in apoptosis signaling). In some embodiments, the biomarker is a biomarker of hypoxia (e.g., high levels of FGF2 in circulation). In some embodiments, the biomarker is a biomarker of transcriptional and/or translational changes (e.g., changes in the ATM/CHK2/p53 pathway, changes in amylase, Flt3-ligand and/or C-reactive protein expression). In some embodiments, the biomarker is a biomarker of epigenomic modifications (e.g., a histone modification, or a change in DNA methylation pattern). In some embodiments, the biomarker is a biomarker of oxidative stress (e.g., a reactive oxygen species or a reactive nitrogen species).

Other biomarkers and potential biomarkers of healthy tissue toxicity have been described. See, e.g., Okunieff et al., Cancer Metastasis Rev. 2008, 27(3): 363-374; Kong et al., Cancer Control 2008, 15(2):140-150; and Pernot et al., Mutation Research 751 (2012) 258-286, each of which is incorporated herein by reference in its entirety for biomarkers that may be used to determine the normal tissue toxicity of a method of treatment described herein. Moreover, any combination of two or more biomarkers may be used to determine the healthy tissue toxicity of a method of treatment described herein.

Therapeutic Efficacy

In some embodiments, the administration of FLASH radiotherapy (e.g., proton FLASH radiotherapy) according to a method described herein results in less healthy tissue toxicity than conventional dose rate radiotherapy while having at least equal anti-tumor efficacy as conventional dose rate radiotherapy. "Anti-tumor activity" may refer to, for example, the prevention of further growth of the tumor, the slowing of tumor growth, the decrease in tumor size, the increase in overall survival, or any other suitable clinical endpoints that indicate therapeutic efficacy.

In some embodiments, administration of FLASH radiotherapy (e.g., proton FLASH radiotherapy) to a tumor according to a method described herein is sufficient to prevent further growth of the tumor for at least 5% longer, at least 10% longer, at least 15% longer, at least 20% longer, at least 25% longer, at least 30% longer, at least 35% longer, at least 40% longer, at least 45% longer, at least 50% longer, at least 60% longer, at least 70% longer, at least 80% longer, at least 90% longer, at least 2 times longer, at least 3 times longer, at least 4 times longer, or at least 5 times longer than standard of care radiotherapy. In some embodiments, administration of FLASH radiotherapy (e.g., proton FLASH radiotherapy) to a tumor according to a method described herein is sufficient to prevent further growth of the tumor for about 5-10% longer, about 10-15% longer, about 15-20% longer, about 20-25% longer, about 25-30% longer, about 30-35% longer, about 35-40% longer, about 40-45% longer, about 45-50% longer, about 50-60% longer, about 60-70% longer, about 70-80% longer, about 80-90% longer, about 2-3 times longer, about 3-4 times longer, about 4-5 times longer, or about 5-10 times longer than standard of care radiotherapy.

In some embodiments, the dose of proton FLASH is equitoxic to the dose of conventional dose rate radiotherapy.

In some embodiments, administration of FLASH radiotherapy (e.g., proton FLASH radiotherapy) to a tumor according to a method described herein is sufficient to induce at least 5% more, at least 10% more, at least 15% more, at least 20% more, at least 25% more, at least 30% more, at least 35% more, at least 40% more, at least 45% more, at least 50% more, at least 6-^e, at least 70% more, at least 80% more, at least 90% more, at least 2 times more, at least 3 times more, at least 4 times more or at least 5 times more tumor regression than standard of care radiotherapy. In some embodiments, administration of FLASH radiotherapy (e.g., proton FLASH radiotherapy) to a tumor according to a method described herein is sufficient to induce about 5-10% more, about 10-15% more, about 15-20% more, about 20-25% more, about 25-30% more, about 30-35% more, about 35-40% more, about 40-45% more, about 45-50% more, about 50-60% more, about 60-70% more, about 70-80% more, about 80-90% more, about 90% more, about 2-3 times more, about 3-4 times more, about 4-5 times more or about 5-10 times more tumor regression than standard of care radiotherapy. In some embodiments, the dose of proton FLASH is equitoxic to the dose of conventional dose rate radiotherapy.

In some embodiments, administration of FLASH radiotherapy (e.g., proton FLASH radiotherapy) to a tumor according to a method described herein delays tumor recurrence for about 2 month to about 6 month, about 6 months to about 9 months, about 9 months to about 12 months, about 12 months to about 15 months, about 15 months to about 18 months, about 18 months to about 21 months, about 21 months to about 24 months, about 2 years to about 3 years, about 3 years to about 4 years, about 4 years to about 5 years, or about 5 years to about 10 years compared to conventional dose rate radiotherapy (e.g., standard of care radiotherapy). In some embodiments, administration of FLASH radiotherapy (e.g., proton FLASH radiotherapy) to a tumor according to a method described herein reduces tumor recurrence by at least about 2 months, at least about 3 months, at least about 6 month, at least about 9 months, at least about 12 months, at least about 15 months, at least about 18 months, at least about 21 months, at least about 2 years, at least about 3 years, at least about 4 years, at least about 5 years, or at least about 10 years compared to conventional dose rate radiotherapy (e.g., standard of care radiotherapy). In some embodiments, the dose of proton FLASH is equitoxic to the dose of conventional dose rate radiotherapy.

Tumor growth and recurrence may be detected using any suitable method known in the art or described herein. For example, tumors may be detected using computer tomography (CT) scanning, magnetic resonance imagining (MRI), positron emission tomography (PET), x-ray, or physical examination. Generally, "tumor recurrence" refers to a tumor becoming detectable again after being undetectable for a prolonged period of time. Tumor growth or regrowth may be measured, for example, as the time required for a tumor to reach a certain volume or size.

EXAMPLES

The examples in this section are provided for illustration only and are not intended to limit the scope of the invention.

Example 1: Experimental Setup for Pre-Clinical Demonstration of FLASH Sparing with Proton Pencil Beam Scanning The aim of this study is to give a thorough characterization of the experimental setup used for this demonstration of FLASH sparing with proton PBS.

Materials and Methods:

The right hind legs of the mice were submerged in a water bath at 13.5 cm depth and irradiated with a 250 MeV FLASH field (138 mice) or a 244 MeV CONV field (154 mice) (see FIG. 1A for an illustration of the set-up). The field size was 2 cm×3 cm and the spot spacing 5 mm. The planned mouse leg dose was 31.7-54.4 Gy (FLASH) or 24.1-40.7 Gy (CONV). The FLASH field was delivered with a requested nozzle beam current of 215 nA. Dose profiles were measured with EBT-XD radiochromic films. For FLASH, the number of monitor units (MU) was reduced with a scaling factor to account for low detection efficiency in the beam monitor chamber. The MU scaling factor was determined daily with an Advanced Markus ionization chamber and once with calorimetry for comparison.

For each FLASH irradiation, the dose rates DR-100% (total dose divided by total field duration) and DR-95% (95% dose in a point divided by shortest time to deliver 95% dose) were determined in the region receiving at least 95% dose. In vivo dosimetry was performed for all FLASH mice with alanine in the beam entrance and a fiber coupled ZnSe:O scintillating crystal with 50 kHz sampling rate right behind the mouse leg (FIG. 1A).

Results

Figure 1B:
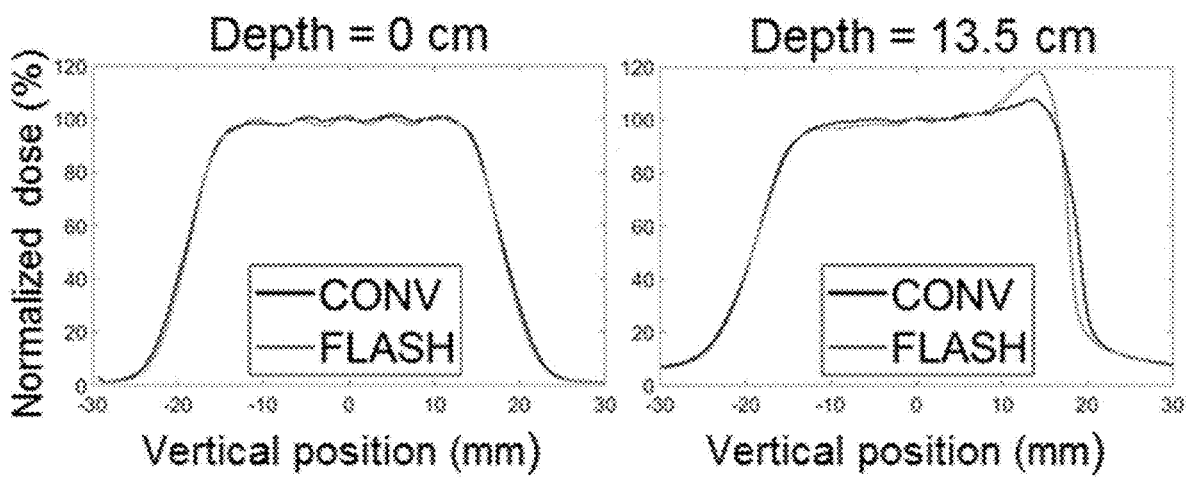

Dose inhomogeneities at the entrance caused by the relatively large spot spacing were decreased at the mouse leg depth (FIG. 1B). The mouse dose was homogenous near the target (mouse foot), but increased by up to 20% near the brass shielding. The MU scaling for FLASH determined by ionization chamber agreed with calorimetry within 0.1%. The dose rate for CONV was 0.4 Gy/s.

Figure 2A:
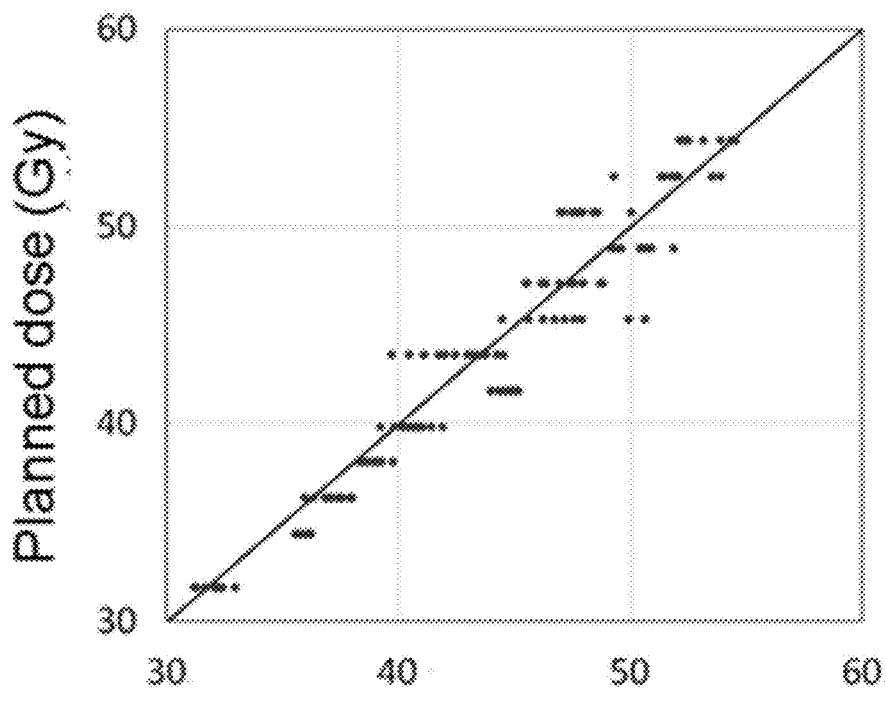
FIGS. 2A and 2B. Individual FLASH mouse doses measured in vivo with alanine at the beam entrance versus the planned mouse dose (FIG. 2A) and versus in vivo doses measured with fiber-coupled scintillating crystals near the mouse foot (FIG. 2B).
Figure 2B:
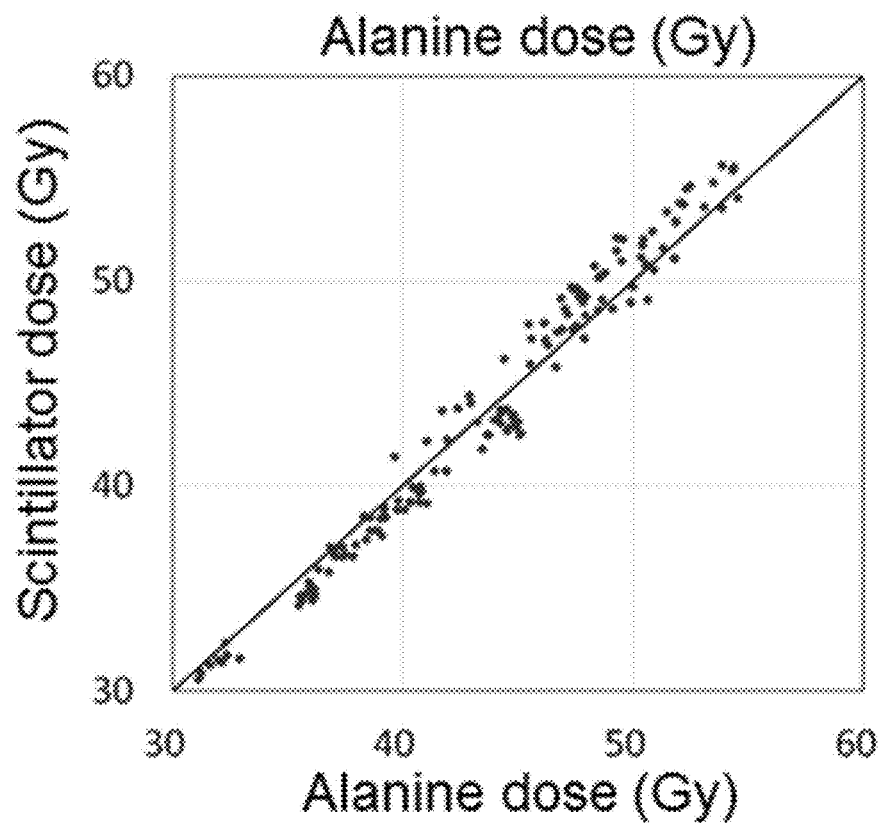

The mean (range) dose rate across all FLASH mice was 80 Gy/s (69-90 Gy/s) for DR-100% and 197 Gy/s (153-240 Gy/s) for DR-95%. While the alanine in vivo FLASH dose varied up to 12% from the planned dose (FIG. 2A), it agreed better with the in vivo scintillator doses (FIG. 2B).

Conclusions

An experimental setup for demonstration of FLASH sparing with proton PBS was established and thoroughly characterized. Alanine in vivo doses agreed better with scintillator in vivo doses than with planned doses, indicating that the observed dose variations between mice with the same planned dose were real.

Example 2: In Vivo Validation and Tissue Sparing Factor for Acute Damage of Pencil Beam Scanning Proton FLASH The aim of the present study was to validate the effect of proton FLASH delivered with a scanning pencil beam in a mouse leg model of acute skin damage, and to quantify the normal tissue sparring factor, the FLASH factor, through full dose response curves.

Materials and Methods

Figure 3A:
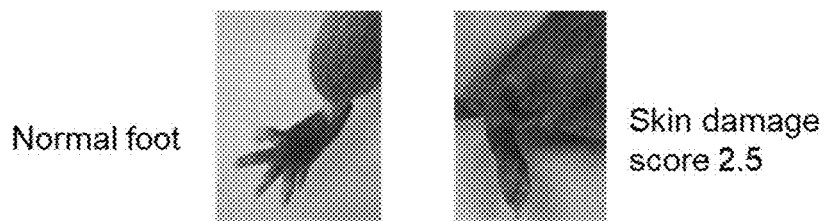
FIG. 3A-3F.
Figure 3B:
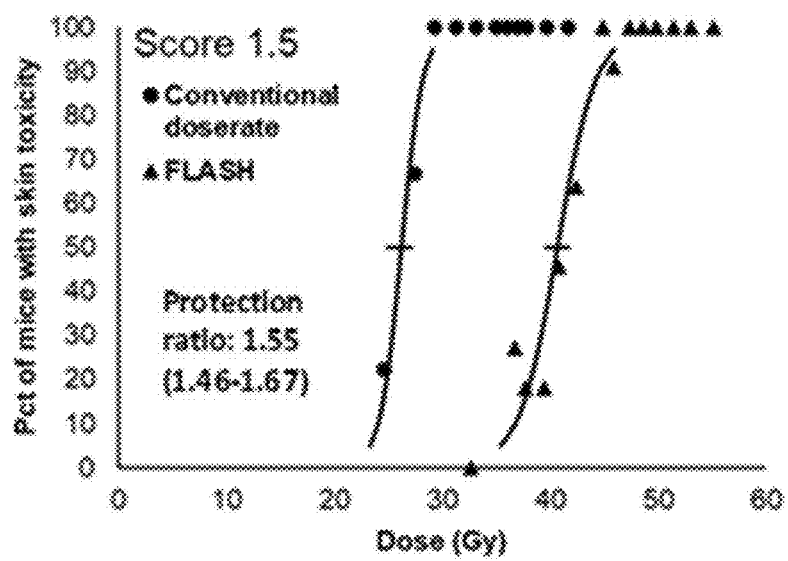
Figure 3C:
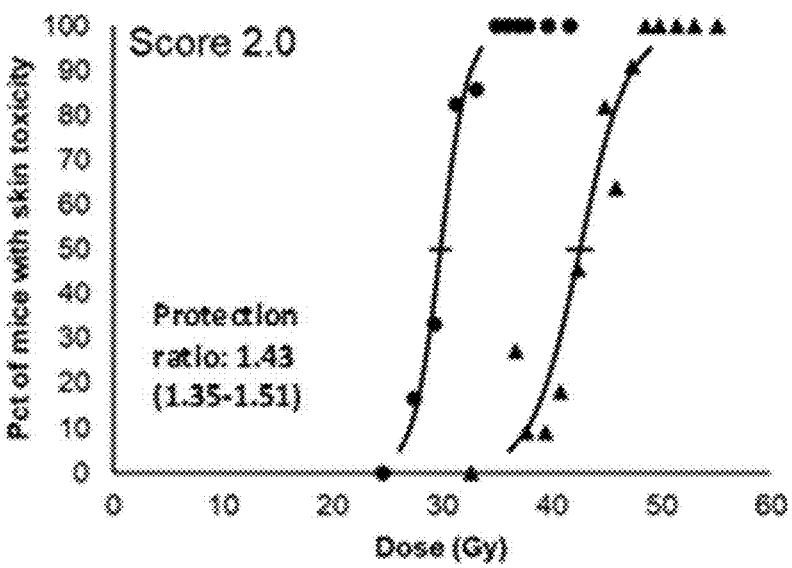
Figure 3D:
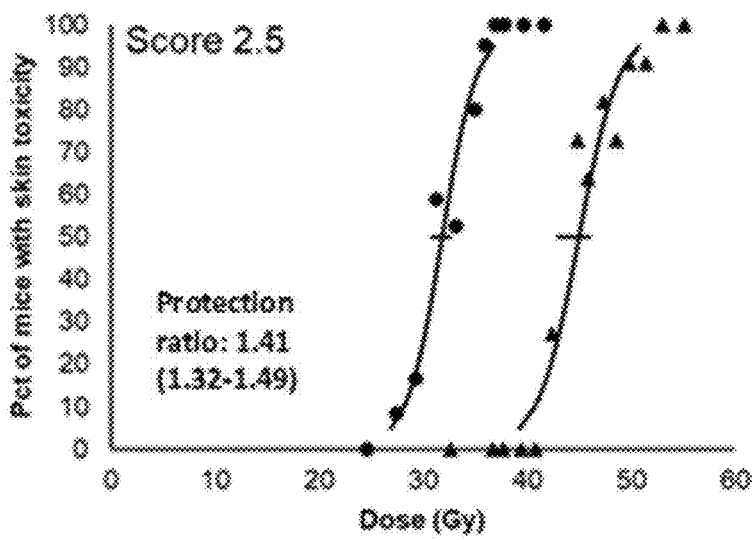
Figure 3E:
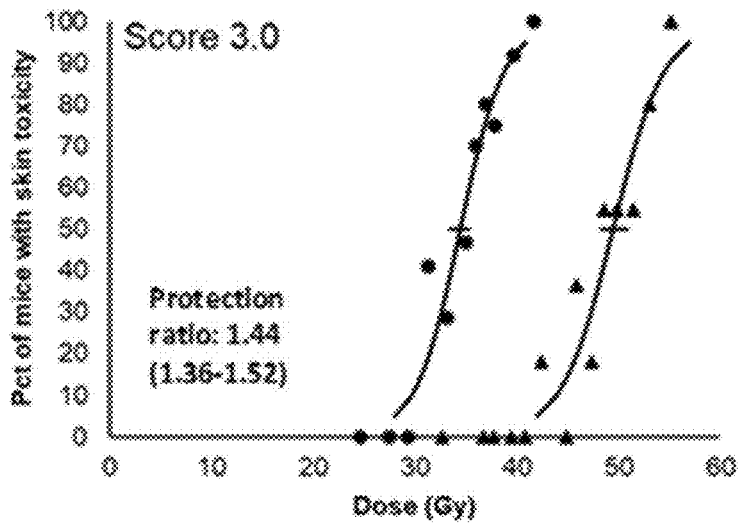
Figure 3F:
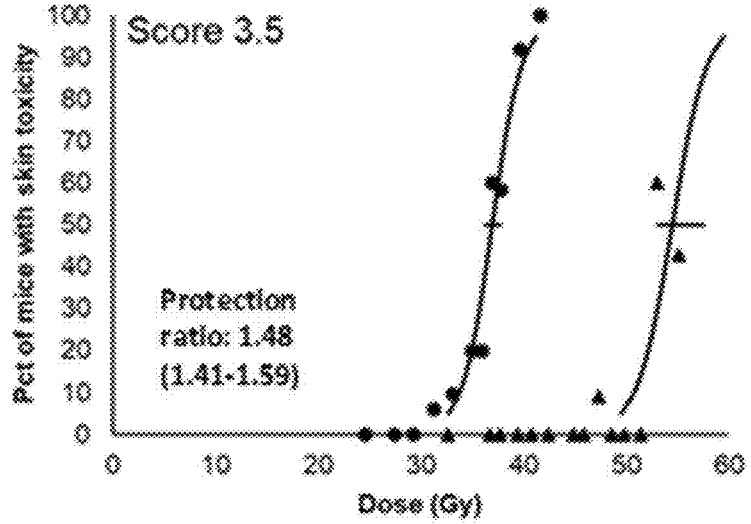

The right hind limb of non-anaesthetized CDF1 mice were irradiated with a single fraction of protons at either conventional or FLASH dose rate. The leg was placed in a water bath, in the entrance plateau (13.5 cm depth). The delivered fields were 2 cm×3 cm to ensure homogeneous dose covering the whole mouse leg. Conventional dose rate was 0.4 Gy/sec (field dose rate) with a beam energy of 244 MeV and the doses were 24.1-40.7 Gy. FLASH dose rate was 69.7-88.7 Gy/s (Field dose rate), with a beam energy of 250 MeV and the doses were 31.7-54.4 Gy. In total, 292 mice were irradiated in four separate experiments, with 7-21 mice per dose point. Alanine pellets were irradiated together with mice in the FLASH arm to verify the delivered dose. The endpoints were the area of acute moist desquamation to the skin of the foot within 25 days post irradiation. (Von der Maase H. Br J Radiol. 1984; 57(680):697-707) (see FIG. 3A for a representative comparison of a normal foot (left) and a skin damaged foot (right, score 2.5).
Results Full dose response curves for five levels of acute damage to skin for both conventional and FLASH dose rate were obtained. A distinct normal tissue sparing effect was observed in the FLASH arm of the study (FIGS. 3B-3F). This effect was similar across all scoring levels with a weighted mean value of 1.46 (Table 1). The MDD50 (dose causing skin toxicity in 50% of mice) values with 95% confidence interval for the five increasing levels of damage to the skin at both dose rates are given in Table 1, as well as the resulting normal tissue sparring factor for the different levels of acute skin damage (ratio of MDD50 for FLASH dose rate to conventional dose rate).

Comparing the time dependency of the damage to the skin between the two modalities revealed similar time pattern, when taking the differential dose dependency into account.

TABLE 1

MDD50 values (dose causing skin toxicity in 50% of mice) with 95% confidence interval for the five increasing levels of damage to the skin at both conventional and FLASH dose rate, and the subsequently Normal tissue sparing factor.

| Level of acute damage | Conventional dose rate MDD50 (95% Conf. Interval) [Gy] | FLASH dose rate MDD50 (95% Conf. Interval) [Gy] | Normal tissue sparing factor |
|---|---|---|---|
| Score 1.5 | 25.7 (24.5-26.6) | 39.8 (38.7-40.8) | 1.55 (1.46-1.67) |
| Score 2 | 29.2 (28.4-30.0) | 41.7 (40.6-42.8) | 1.43 (1.35-1.51) |
| Score 2.5 | 31.1 (30.1-32.0) | 44.0 (42.1-45.1) | 1.41 (1.32-1.49) |
| Score 3 | 33.7 (32.8-34.5) | 48.4 (47.2-49.8) | 1.44 (1.36-1.52) |
| Score 3.5 | 36.2 (35.5-37.0) | 53.4 (52.0-56.2) | 1.48 (1.41-1.59) |

Conclusions

This study validates the normal tissue sparing effect of proton FLASH when delivered with pencil beam scanning. Full dose response curves for acute skin damage in a mouse leg model were obtained, which enabled the quantification of the normal tissue sparing factor for proton FLASH. A 41-55% higher dose was required to give the same biological response when using FLASH dose rates compared to the conventional dose rates.

Example 3: Soft Tissue Toxicity with FLASH

Figure 4A:
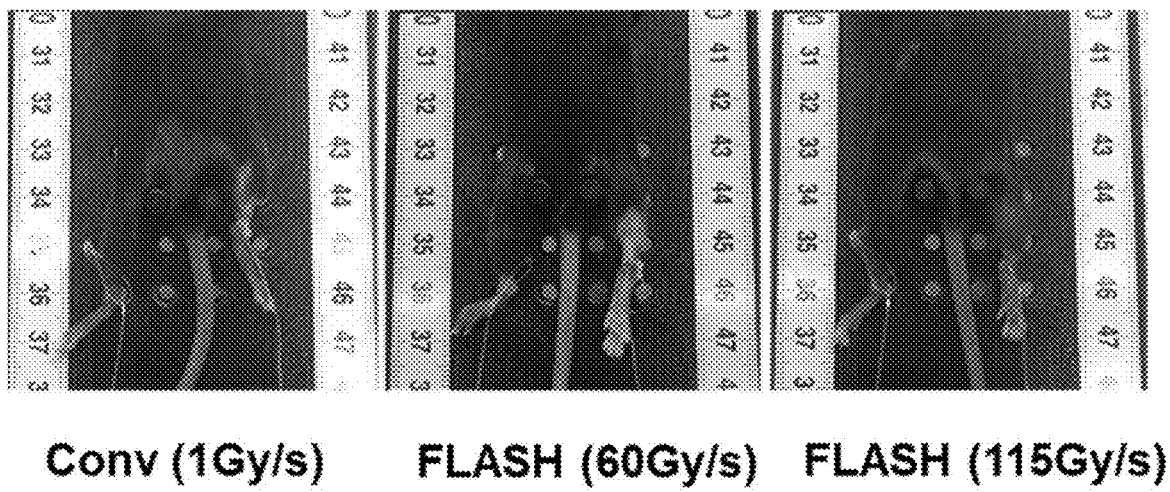
FIGS. 4A-4D.
Figure 4B:
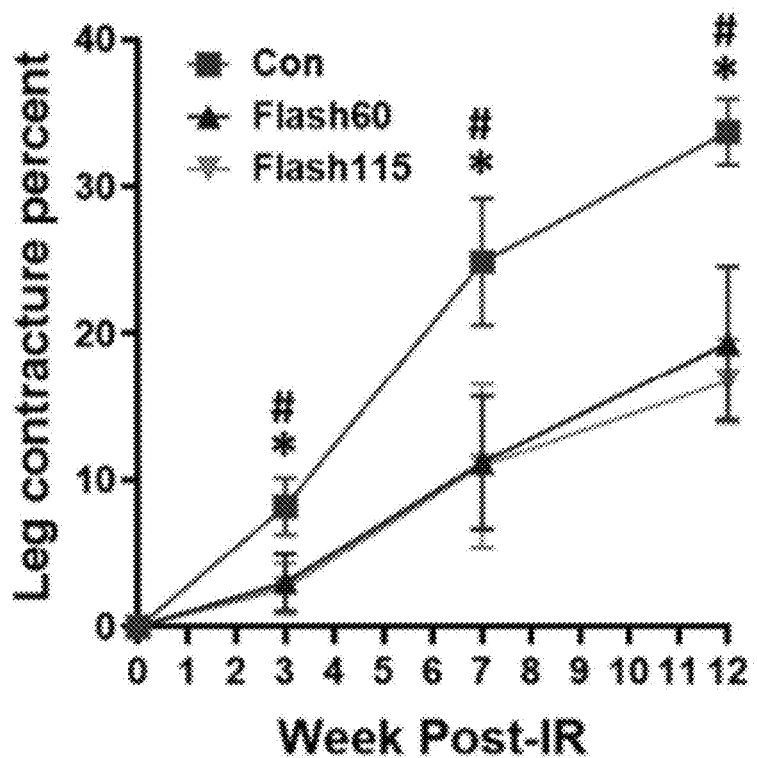
Figure 4C:
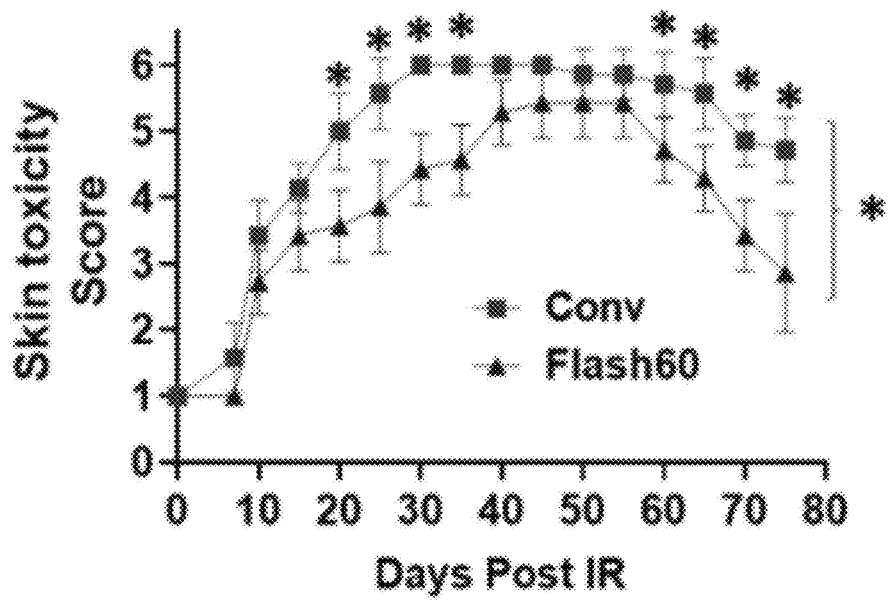
Figure 4D:
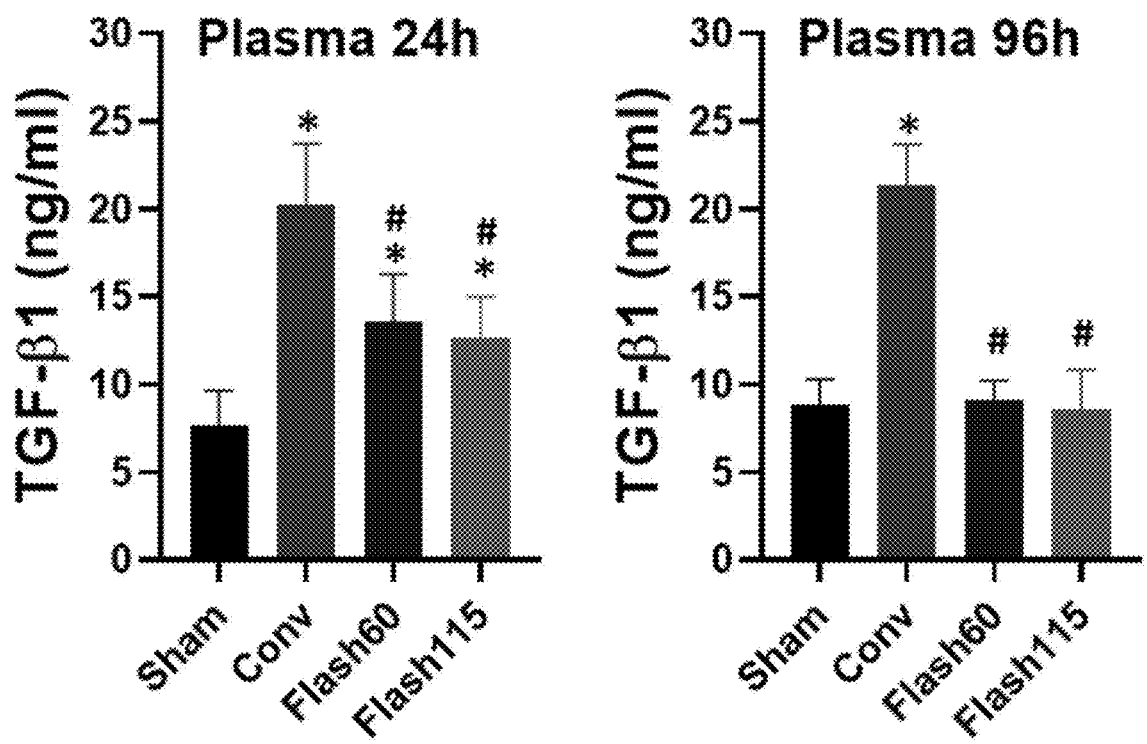

The aim of this study was to evaluate the soft tissue toxicity of FLASH.
Materials and Methods Unshaved right hind leg of 10-week old female C57B1/6j mice treated with 35 Gy of conventional proton therapy, FLASH proton therapy at 60 Gy/s, or FLASH proton therapy at 115 Gy/s. Soft tissue toxicity was assessed by measuring skin toxicity and leg contracture at 3 weeks, 7 weeks, 12 weeks after radiation. Leg contracture of the mice was measured using a 3D printed jig at 3, 7 and 12 weeks post irradiation. The un-irradiated (Sham) left hind leg of each mouse was used as control to calculate the leg contracture score. The extension of the sham (left) and irradiated (right) leg was measured under a 0.1N force. Percentage leg contracture was calculated as: [1-(leg extension irradiated leg/leg extension sham leg)]*100. Skin toxicity was scored every 5 days until the end of the study using a previously published skin toxicity grade scale.
Results Representative images illustrating leg contracture are shown in FIG. 4A. Treatment with FLASH proton therapy (at either dose) resulted in a 50% reduction in muscle contracture and skin toxicity compared to treatment with conventional proton therapy (FIG. 4B and FIG. 4C), suggesting that FLASH proton therapy reduces muscle and skin toxicity compared to conventional proton therapy.

Example 4: FLASH Efficacy in In Vivo Models of Head and Neck Cancer

Figure 5A:
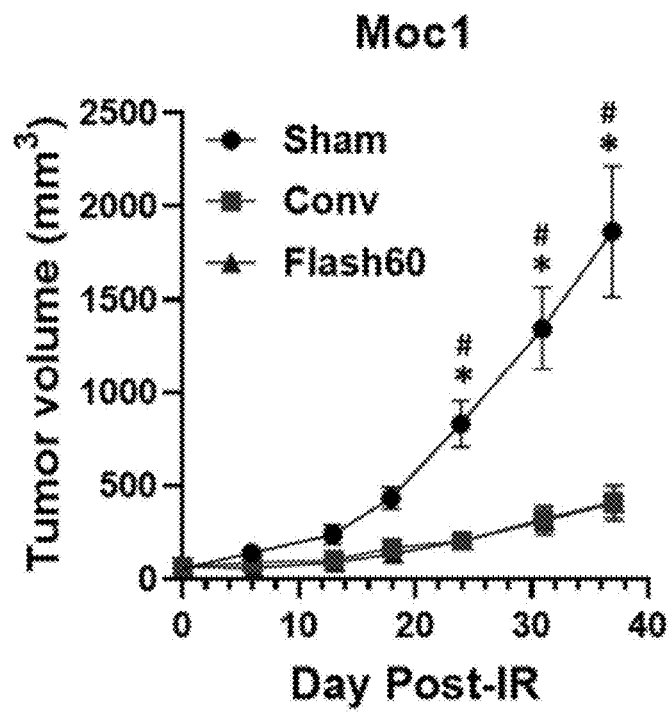
FIGS. 5A and 5B. Effects of FLASH and CONV proton therapy in mouse models of indolent (FIG. 5A) and aggressive (FIG. 5B) head and neck tumors implanted subcutaneously in the mouse limb.
Figure 5B:
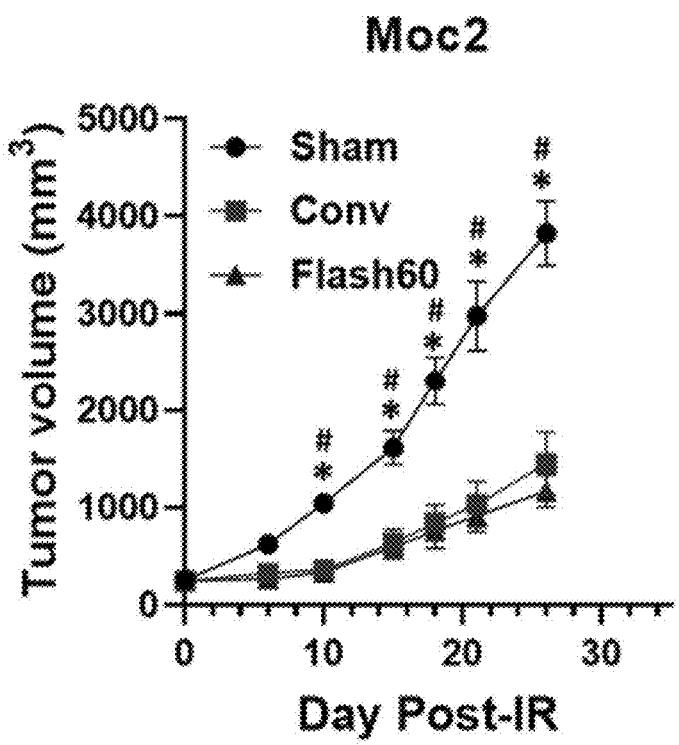

The purpose of this study was to evaluate the efficacy of FLASH radiation in an in vivo model of head and neck cancer.
Materials and Methods Two subcutaneous models of head and neck cancer was used in this study. Eight-week-old female C57B1/6j mice per group were injected subcutaneously into their shaved right hind leg with either $2 \times 10^5$ MOC2 or $2 \times 10^6$ MOC1 mouse oral carcinoma cell lines. Twenty-one-day post injection, tumors were measured with calipers and mice were randomized to create 3 groups of equal average tumor size. The tumor bearing hind legs were irradiated as described above with an absolute dose of 15 Gy and dose rate of 1 Gy/s (Conv) or 60 Gy/s (Flash60). Tumor volume was determined by caliper measurement every 4 days for MOC2 (total of 28 days post irradiation) and once a week for MOC1 (total of 37 days post irradiation). Volume was calculated as Tumor volume (mm3)=(Width tumor2 (mm)×Length tumor (mm))/2.
Results Data are shown in FIGS. 5A-5B. Both conventional proton therapy and FLASH proton therapy slowed tumor growth compared to sham irradiated controls. The tumor growth, either using indolent MOC1 (FIG. 5A) or aggressive MOC2 (FIG. 5B) cell lines, in mice treated with conventional proton therapy was comparable to the tumor growth in mice treated with FLASH proton therapy. TGF-B1 levels, which has been widely reported as a marker of tissue damage, were decreased in mice plasma when using FLASH rate/dose (either at 60 Gy/s and 115 Gy/s) compared to conventional showing a systemic response (FIG. 5C).

Example 5: FLASH Efficacy in In Vivo Models C3H

The purpose of this study was to evaluate the efficacy of FLASH radiation in tumor control and assessing skin toxicity using an in vivo model of mouse mammary carcinoma
Materials and Methods C3H mouse mammary carcinoma cell line was injected subcutaneously in the foot of the C57B1/6j mice. Mice were irradiated as described in Example 1 (FIG. 1A). Tumor control was assessed as complete disappearance of tumor within 3 months after treatment. Skin toxicity was assessed as previously described in Example 2. FIG. 6C shows a mouse leg bearing a subcutaneous C3H tumor.

Results

Figure 6A:
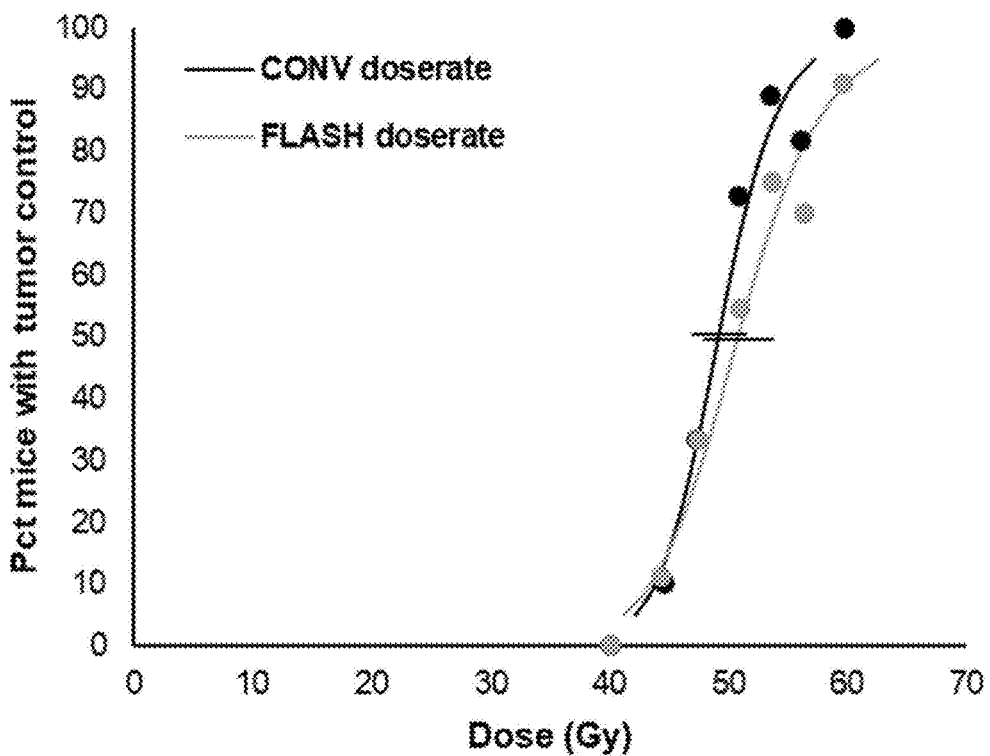
FIGS. 6A-6D. FIGS., 6A and 6B show the effect of FLASH and CONV proton therapy in mouse bearing C3H mouse mammary carcinoma tumors.
Figure 6B:
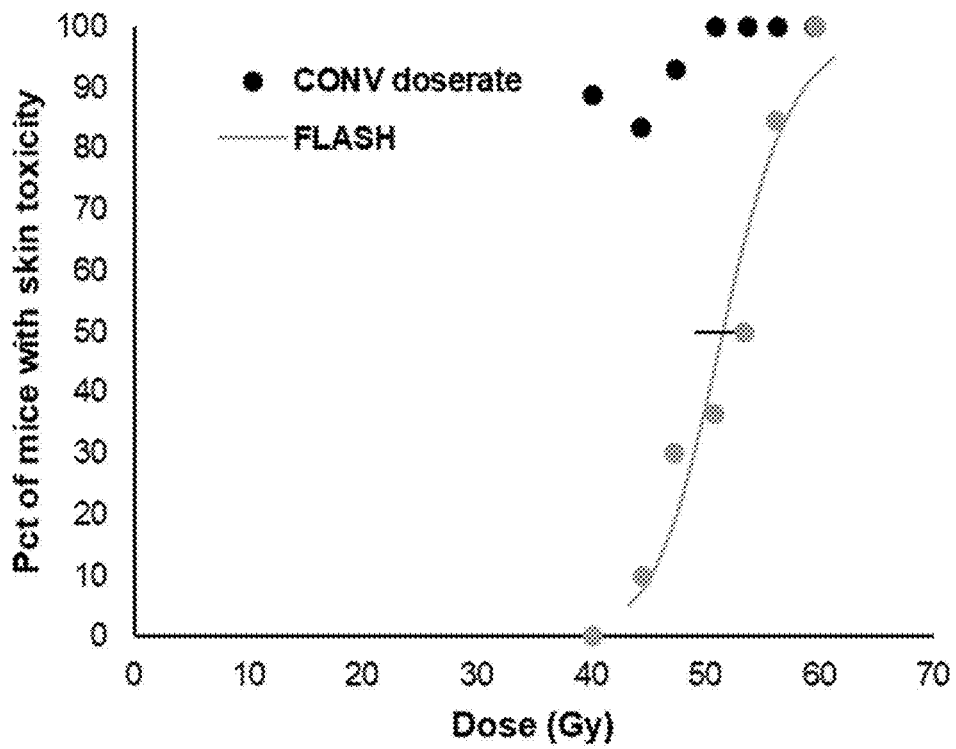
Figure 6C:
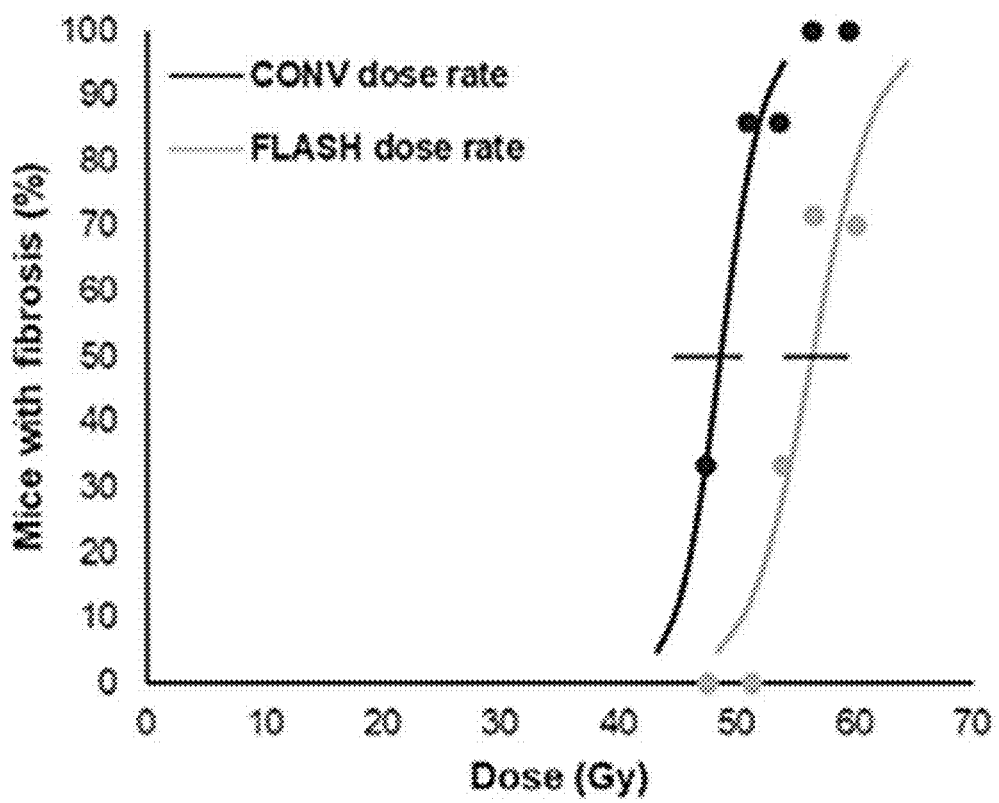
Figure 6D:
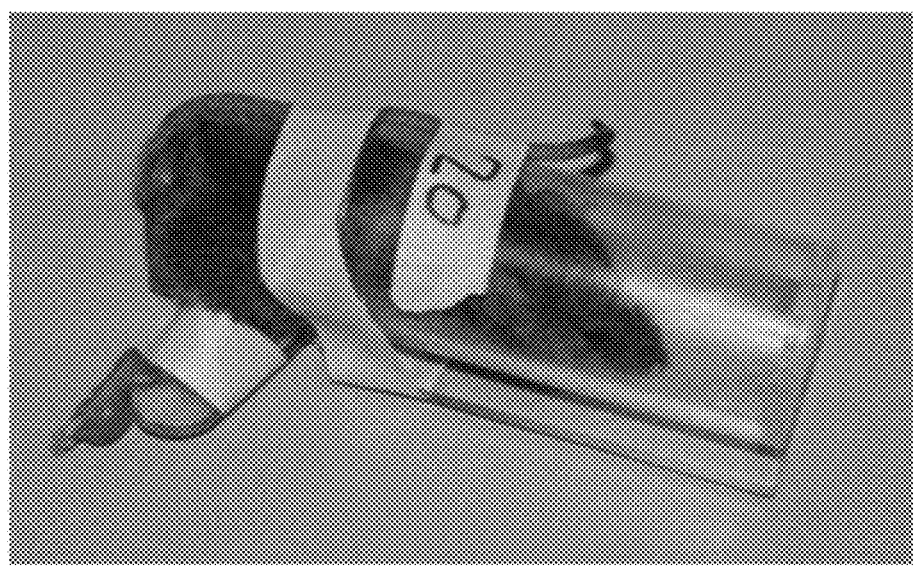

Data are shown in FIG. 6A and FIG. 6B. Both conventional proton therapy and FLASH proton therapy showed comparable tumor control (FIG. 6A) while showing a sparing effect on skin toxicity (FIG. 6B).

Example 6: Neurological Toxicity with FLASH

Figure 7A:
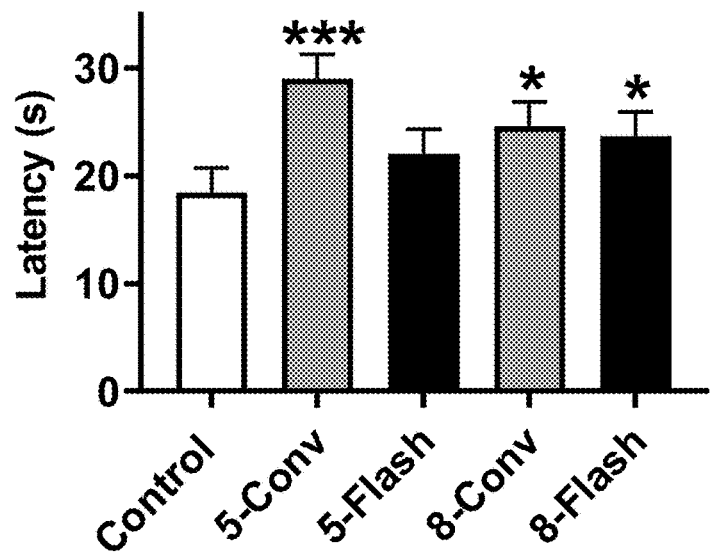
FIGS. 7A-7D show neurological toxicity with FLASH and CONV proton therapy assessed with the radial water maze latency.
Figure 7B:
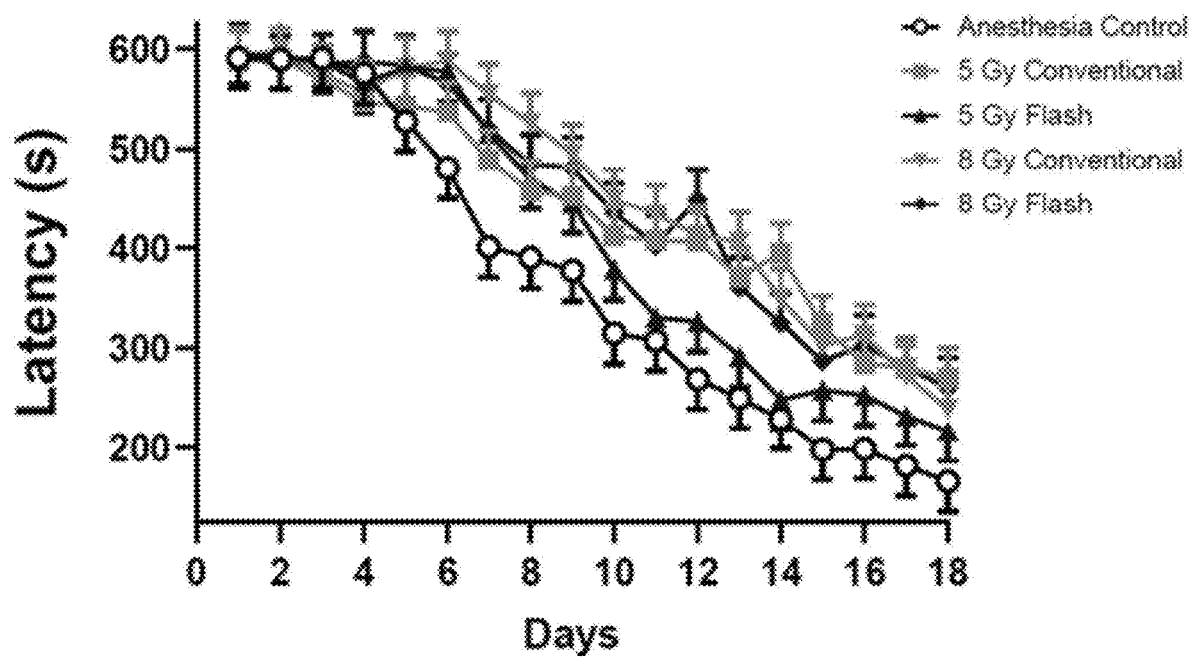
Figure 7C:
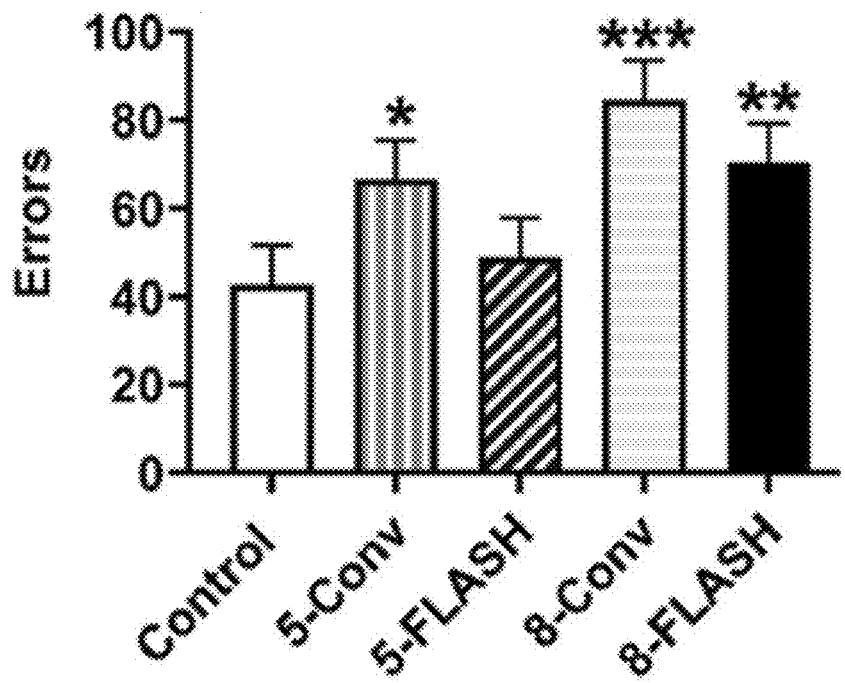
Figure 7D:
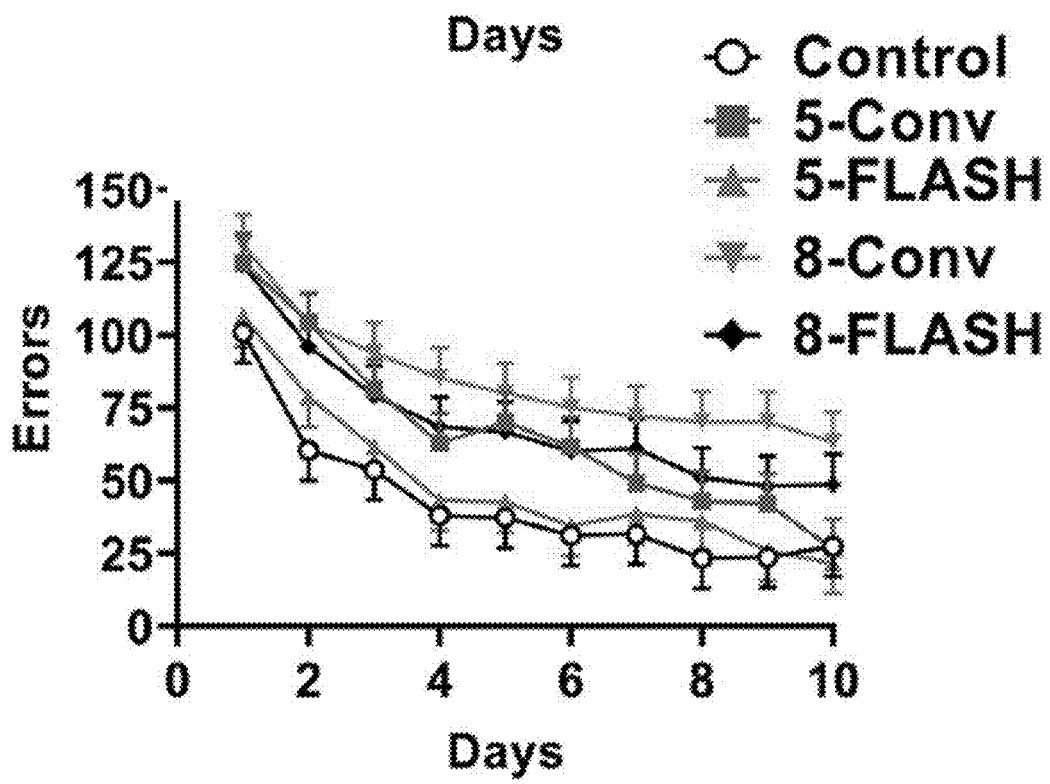

The aim of this study was to evaluate the neurological toxicity of FLASH.
Materials and Methods To assess neurological toxicity, neonatal rats Sprague Dawley rats (P11) were treated with either 5 Gy conventional proton therapy, 5 Gy FLASH proton therapy, 8 Gy conventional proton therapy, or 8 Gy FLASH proton therapy. Behavioral and cognitive function were tested using the Radial Water Maze from P89 to P95 and the Cincinnati Water Maze-Mirror from P71 to P88.
Results Data are shown in FIGS. 7A and 7B. 5 Gy of FLASH proton showed a sparing effect on working memory as evaluated by the Radial Water Maze and with the mirror image Cincinnati Water maze compared to 5 Gy of conventional proton therapy. On Day-1 the 5-Cony ($p<0.0001$), 8-Conv ($p<0.02$), and 8-FLASH ($p<0.03$) groups were slower in locating the platforms than controls, while there was no difference between the 5-FLASH group compared with controls (FIG. 7A). Regardless of group, there was an increase in latency to locate the platform over trials. For errors per trial on Day-1, compared with controls the 5-Cony ($p<0.002$) and the 8-Cony ($p<0.03$) groups made more errors and there were no differences in the FLASH groups (FIG. 7B). Rats committed more errors over trials. No effects of sex or other interactions were found for latency or errors. For Day-2 latency, the 5-FLASH ($p<0.04$) and 8-FLASH ($p<0.03$) groups were slower at locating the platform than controls, while there were no differences between controls and the other groups (FIG. 7C). There was an increase in latency to locate the platform over trials, $p<0.0001$, regardless of group (not shown). On day-2, there were no differences in errors per trial between the irradiated groups and controls (FIG. 7D). There was a significant interaction of exposure group×sex×trial. For females there were no differences between irradiated groups and controls on any trials. For males the 5-FLASH ($p<0.0007$) and 8-Conv ($p<0.0004$) groups had more errors on trial-7 than controls. No other trial showed significant group differences. There was an increase in errors to locate the platform over trials, $F(7, 1041)=73.92$, $p<0.0001$, regardless of group.

Figure 8A:
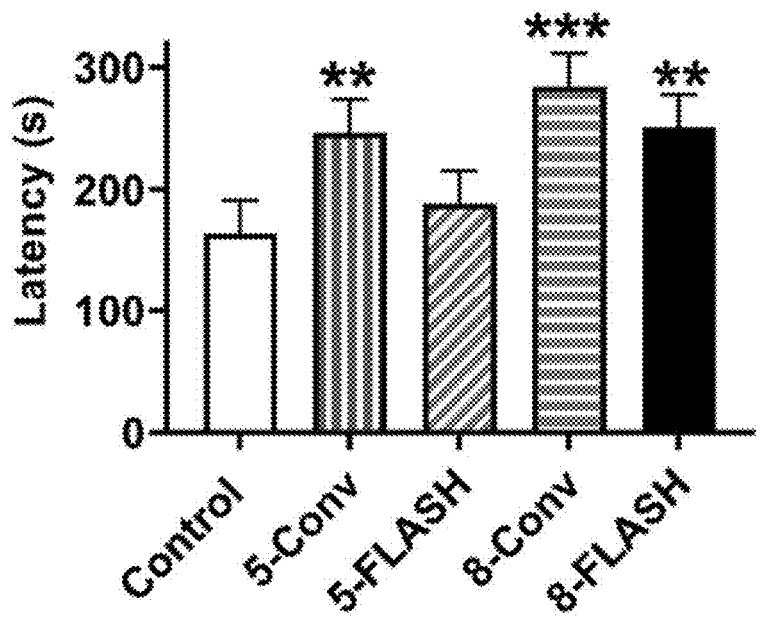
FIGS. 8A-8D show neurological toxicity with FLASH and CONV proton therapy assess with the Cincinnati water maze mirror version.
Figure 8B:
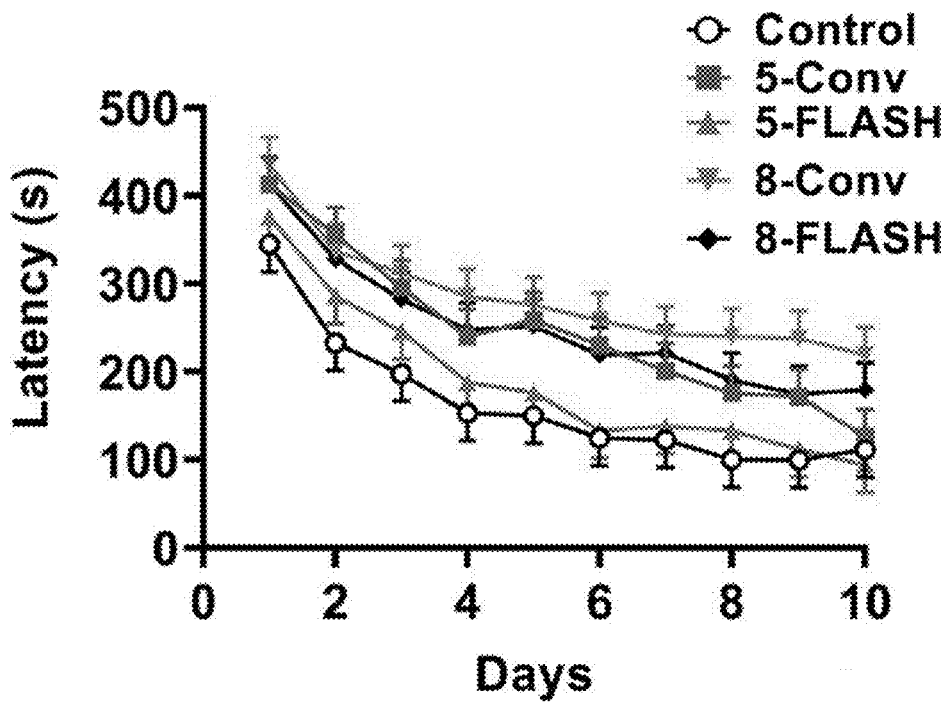
Figure 8C:
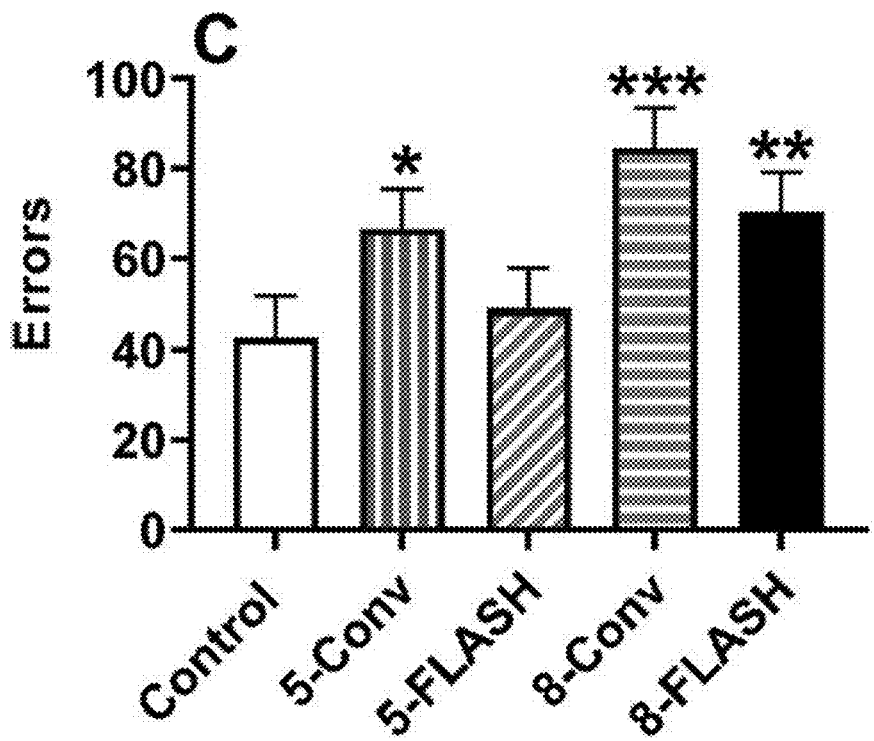
Figure 8D:
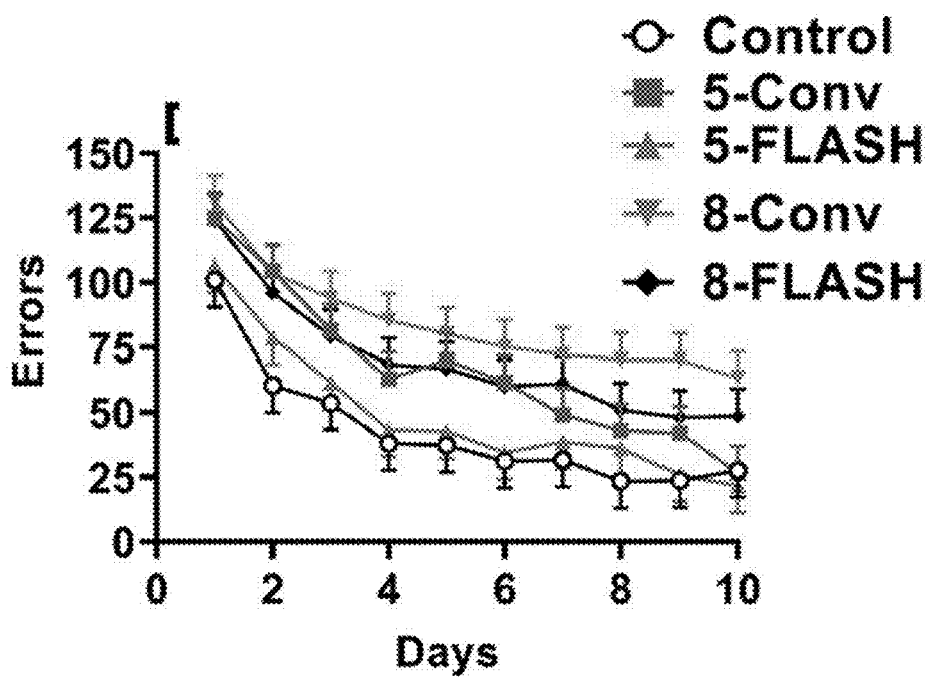

Data are shown in FIGS. 8A and 8B. 5 Gy of FLASH proton showed a sparing effect on working memory as evaluated by the Cincinnati water mase-mirror compared to 5 Gy of conventional proton therapy For latency to the platform, the 5-Cony ($p<0.008$), 8-Cony ($p<0.0002$), and 8-FLASH ($p<0.006$) groups were slower at locating the platform than the controls, but there was no difference between the 5-FLASH group and controls (FIG. 8A). The latency to locate the platform decreased over days (FIG. 8B). There was no significant sex main effect, but there was a sex×day interaction. Females located the platform faster on days 1 and 2 than males. No other interactions were significant. Similar to latency, for errors the number of errors were greater in the 5-Cony ($p<0.02$), 8-Cony ($p<0.0001$), and 8-FLASH ($p<0.008$) groups compared with controls with no difference between the 5-FLASH group and controls (FIG. 8C). The number of errors decreased over days for all groups (FIG. 8D). No sex differences or other interactions were significant. These data indicate that 8 Gy of FLASH radiation is equivalent to 5 Gy of conventional dose rate therapy.

Example 7: FLASH Efficacy in In Vivo Models of Glioblastoma

Figure 9A:
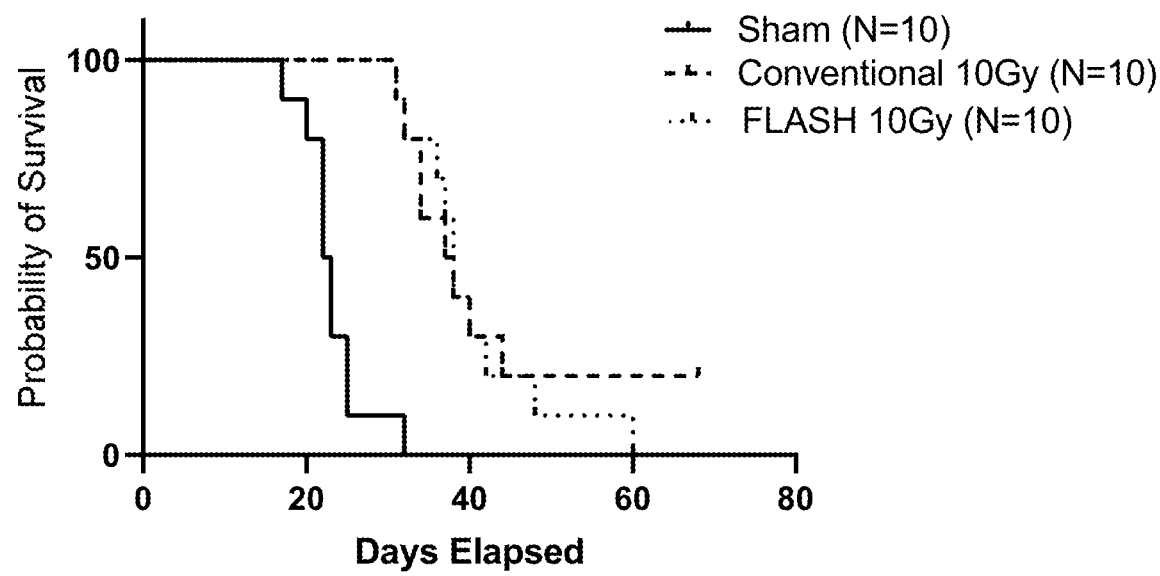
FIG. 9A-9D show the effects of FLASH and CONV proton therapy in two mouse models of glioblastoma (GBM).
Figure 9B:
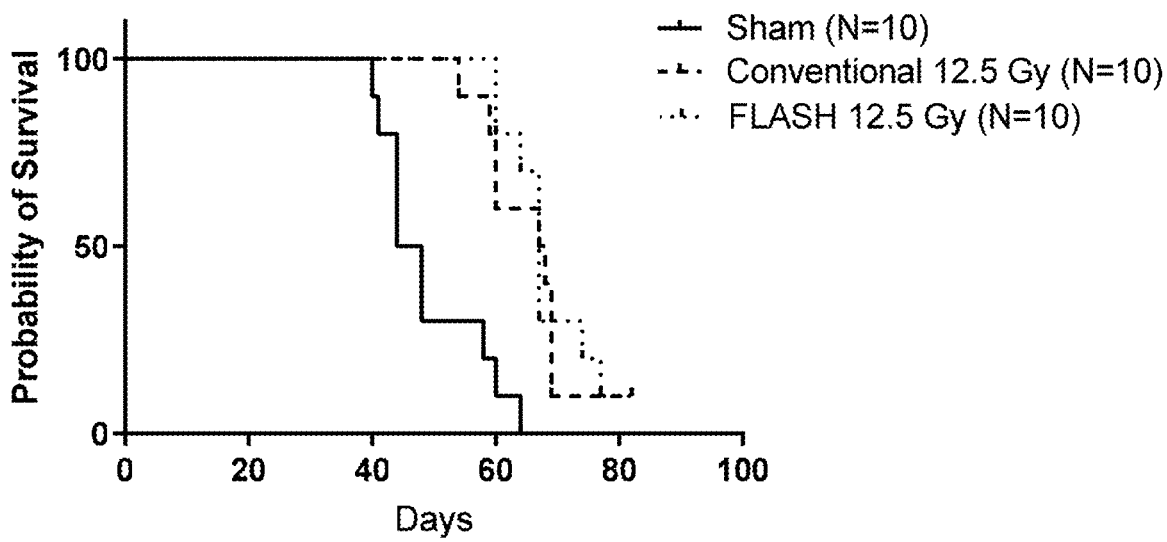
Figure 9C:
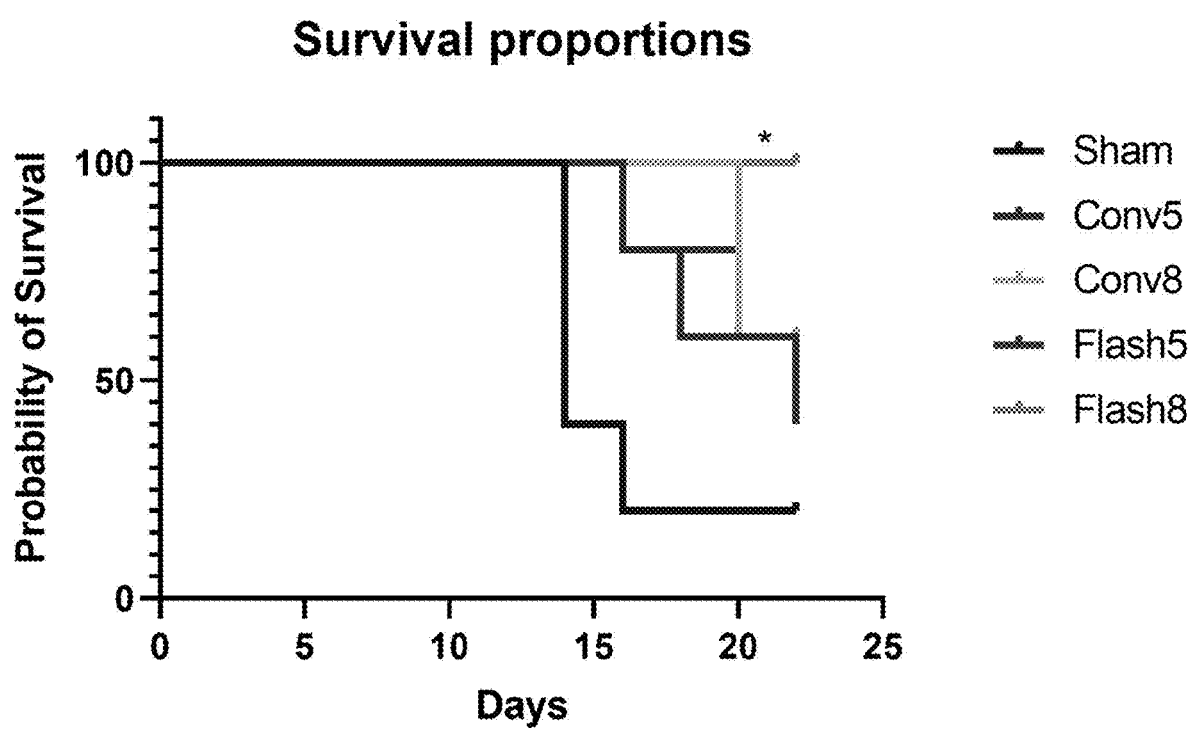
Figure 9D:
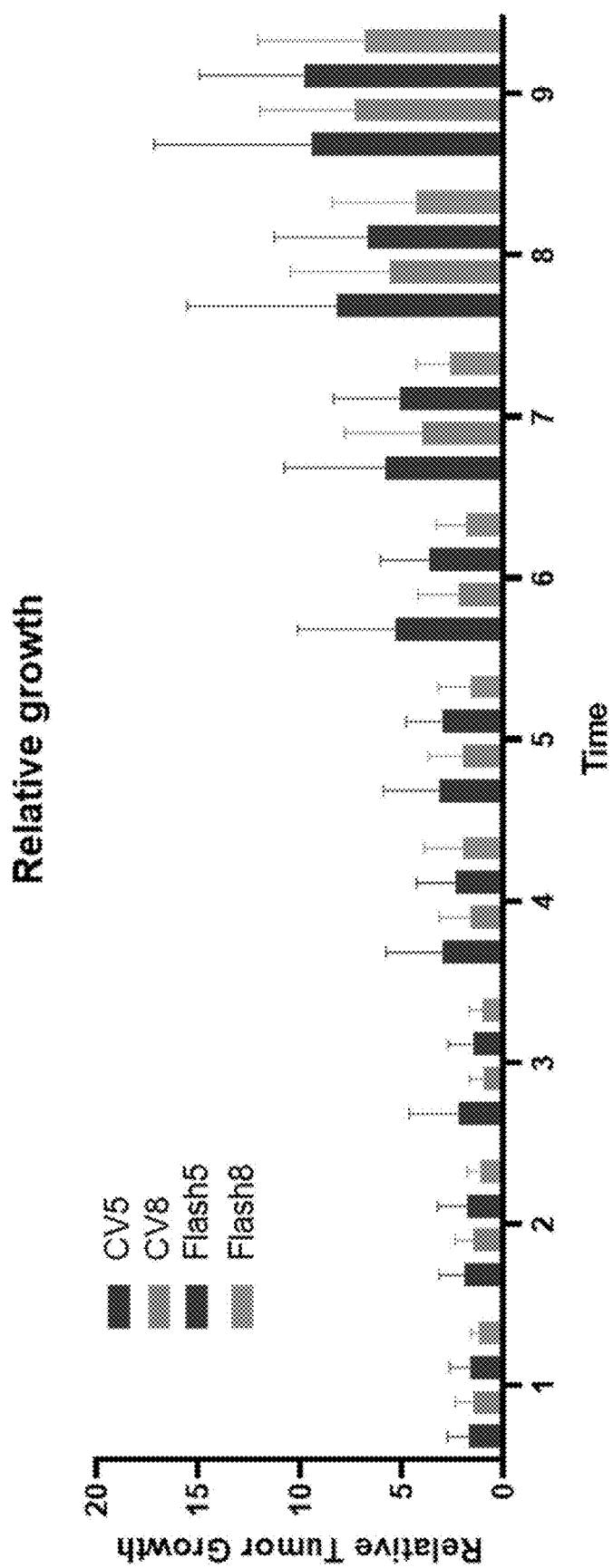

The aim of this study was to evaluate the efficacy of FLASH on two different models of glioblastoma.
Materials and Methods An orthotopic or subcutaneous GL261 syngeneic model of glioblastoma and a genetically engineered PDGFRA-D842V-dnp53 model of glioblastoma were used in this study. For the orthotopic model, 100,000 GL26L1-luciferase cells or PDGFRA-D842V-dnp53-luciferase cells were injected in the striatum of the mice and imaged by IVIS and/or MRI at day 5 after transplant to confirm tumor growth. Mice were randomized and treated with either 10 Gy or 12.5 Gy of conventional proton therapy (n=10) or with 10 Gy or 12.5 Gy of FLASH proton therapy at 100 Gy/s. Survival was monitored. For the syngeneic GL261 subcutaneous flank tumor model, 100,000 GL26L1-luciferase cells were mixed 1:1 with Matrigel and implanted subcutaneously into C57/BL6 mice. Tumor volume was measured by calipers and animals were randomized based when they reached between 50 to 80 mm$^3$. Mice were treated with 5 Gy or 8 Gy at both conventional and Flash dose rate. Tumor volume was measured throughout the study and Survival was monitored.
Results:

Data for the orthotopic model are shown in FIGS. 9A and 9B. Survival in all treatment groups was prolonged compared to the sham irradiated control mice (p-value<0.001, log-rank test). FLASH therapy with 10 Gy (FIG. 9A) or 12.5 Gy (FIG. 9B) at 100 Gy/s and conventional dose rate proton therapy at 10 Gy resulted in comparable survival. Tumor growth in these GBM models grown subcutaneously and treated with 5 Gy and 8 Gy of Conv and Flash were compared. Data shown in FIGS. 9C and 9D indicate that 8 Gy of FLASH tended to be efficient at reducing tumor growth than 5 Gy. However, as shown in Example 6 above, these doses are equitoxic.

Example 8

Figure 10A:
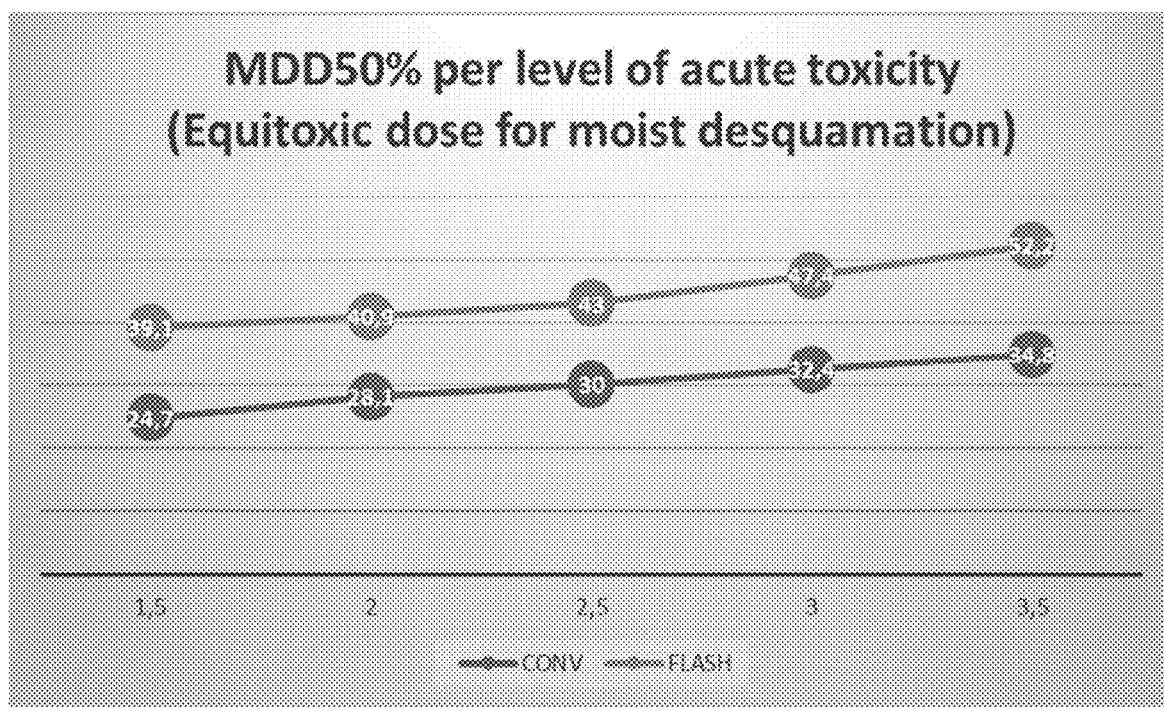
FIG. 10A-10C show tumor control at equitoxic doses for moist desquamation (the dose to produce moist desquamation in 50% of mice; MDD50%).

Based on data from FIG. 3, we determined That the equitoxic dose for grade 3,5 moist desquamation was 34.8 Gy for conventional dose rate therapy and 52.2 Gy for FLASH dose rate therapy. The equitoxic dose for grade 2 moist desquamation was 30 Gy for conventional dose rate therapy and 43 Gy for FLASH dose rate. The tumor control effect of the equitoxic doses as assessed previously in Example 5 (FIG. 6A) was compared. Results are shown in FIG. 10.

Figure 10B:
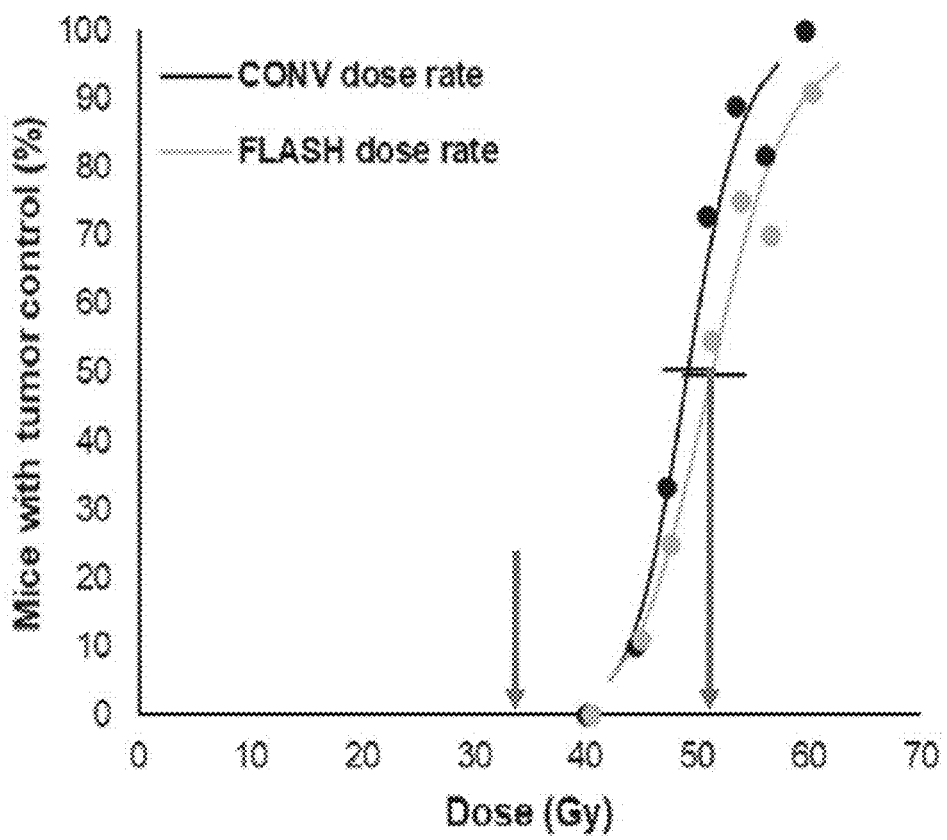
Figure 10C:
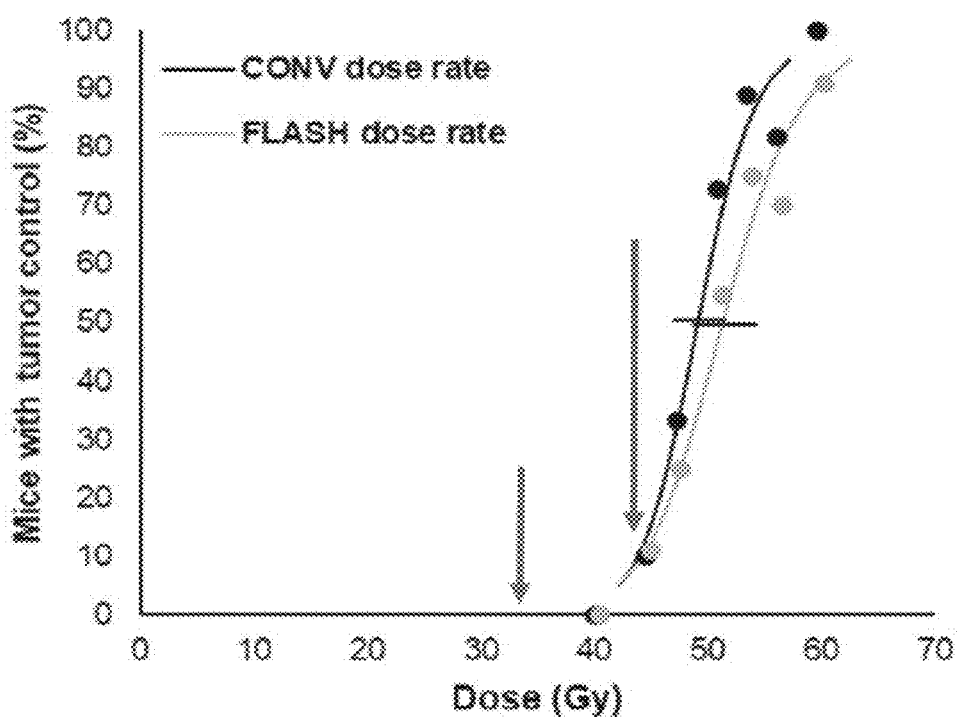

As shown in FIG. 10B, tumor control rose from 0% (conv) to 50% (FLASH) at the equitoxic dose for grade 3,5 moist desquamation (34.8 Gy Conv vs 52.2 Gy FLASH). At equitoxic dose for grade 2 moist desquamation (30 Gy Conv vs 43 Gy FLASH), tumor control raises approx. from 0% (conv) to 10% (FLASH) (FIG. 10C)

Example 9: Tissue-Sparing Effects of High does Rate Radiation

External radiation is a treatment modality aimed at delivering energy on a given target, typically a tumor tissue. This energy is delivered by a device at a given dose rate in Gy/second. Traditional devices used in clinics display a dose rate ranging from 0.01 to 1 Gy/sec. Currently, this dose rate is named "conventional dose rate". Without wishing to be bound by theory, it is believed that FLASH radiation, typically ranging above 40 Gy/sec, is associated with lower side effects on the healthy tissue while the anti-tumor is equivalent to conventional dose rate.

A dose rate escalation study of FLASH was carried out on a pre-clinical model of skin toxicity. Mice were irradiated with 39.3 Gy radiation at the indicated dose rates and tissue toxicity was assessed two weeks later. Tissue toxicity was scored as follow: Score 1.5: mild damage, Score 2.5: medium damage, Score 3: severe damage.

Figure 11A:
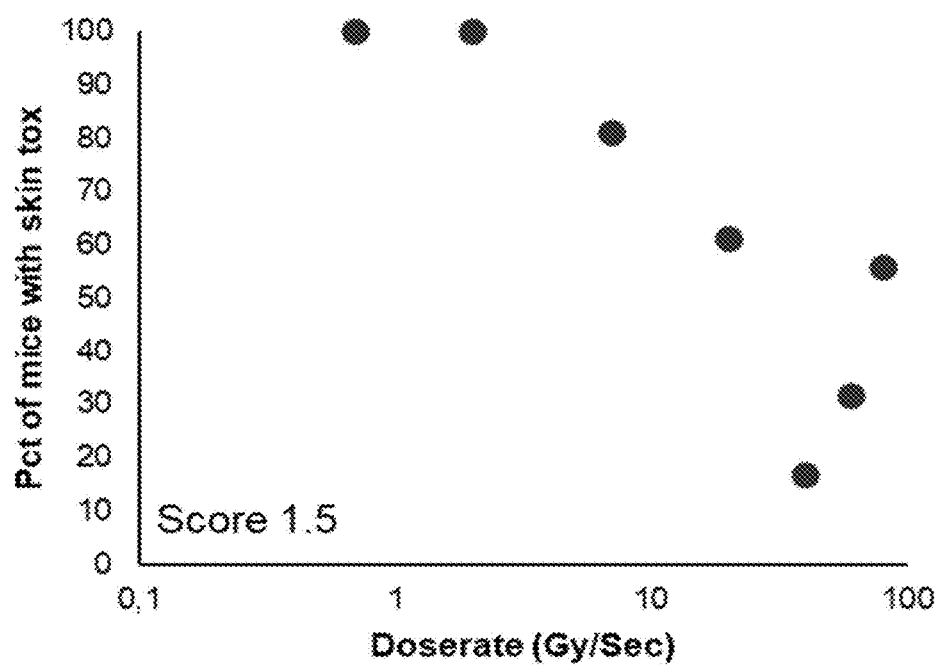
FIGS. 11A-11C: Doserate-response of different levels of acute skin toxicity. Percentage of mice in each dose rate group with acute damage to the skin at different levels (Score 1.5: mild damage, FIG. 10A; Score 2.5: medium damage, FIG. 10B; Score 3: severe damage, FIG. 10C). All mice were irradiated with same dose, 39.3 Gy.
Figure 11B:
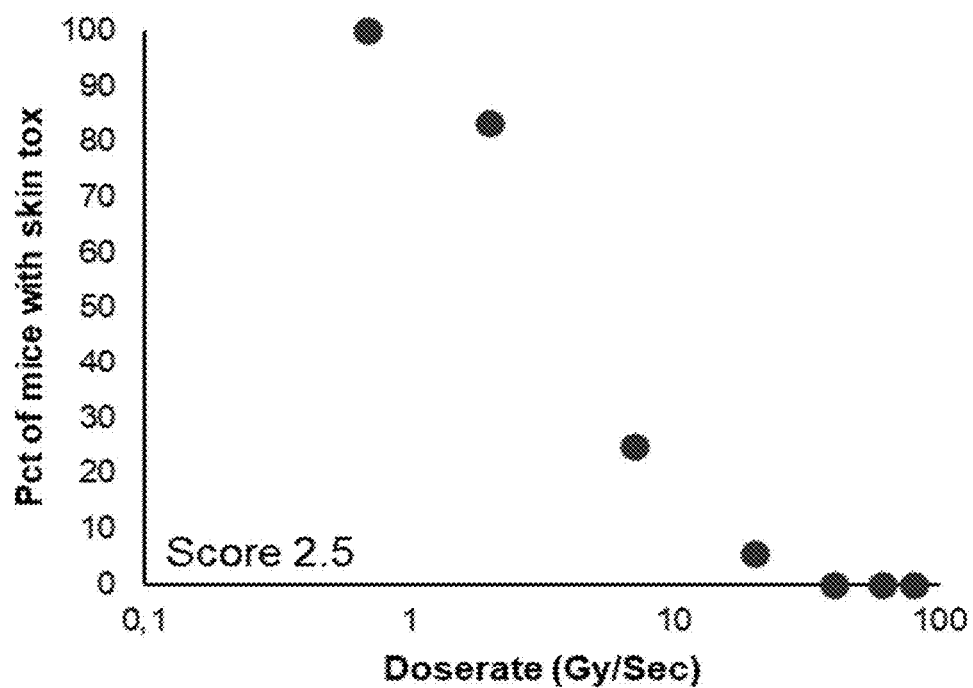
Figure 11C:
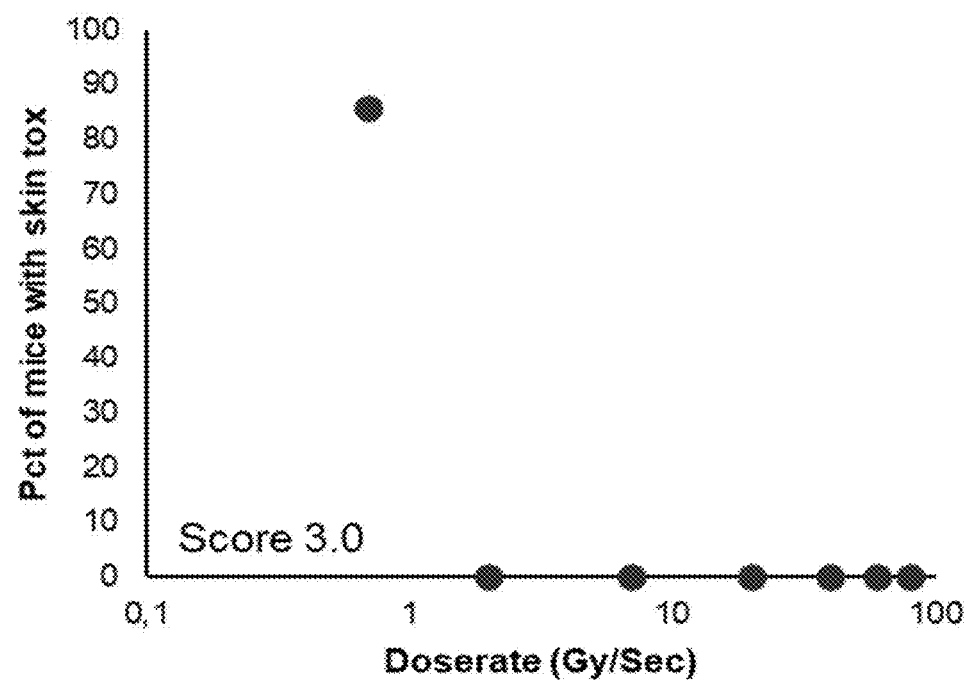

Results are shown in FIGS. 11A-11C. A sparing effect on the healthy tissue at dose rates between 1 Gy/sec and 40 Gy/sec was observed. This dose rate range classically defines conventional dose rate and UHDR respectively. It is hypothesized that this dose rate range is sufficient to reduce healthy tissue toxicity.

A 40% reduction of the incidence of grade 1.5 skin toxicity was observed at dose rates of 8 Gy/sec or higher. A 20% and 75% reduction of the incidence of grade 2 skin toxicity at 2 and 8 Gy/sec respectively. A complete abrogation of grade 2.5 skin toxicity was observed at 2 Gy/sec or higher. The data show that the level of skin toxicity is highly sensitive to dose rate and that the Flash effect differs at the diverse toxicity levels.

Example 10: FLASH and Conventional Dose Rate Therapy have Comparable Lung Cancer Control Materials and Methods An orthotopic Lewis lung carcinoma (LLC) was used in this study. 20,000 LLC-mCherry tumor cells were injected into the left lung lobe of C57BL/6 mice. 15 days after the tumor injection, the lungs of the tumor-bearing mice were irradiated with protons to a total dose of 18 Gy at conventional dose rate (1 Gy/s) and Flash dose rate (60 gy/s). Mice were sacrificed on day 20 (day 5 after irradiation, 3 mice per group) and 23 (day 8 after irradiation, 5 mice per group) post tumor inoculation and tumor sizes were measured using calipers. Tumor Volume was calculated using the formula: $V=\frac{1}{2}*L*W^2$ (L=Length, W=Width of the tumor).

Results

Figure 12A:
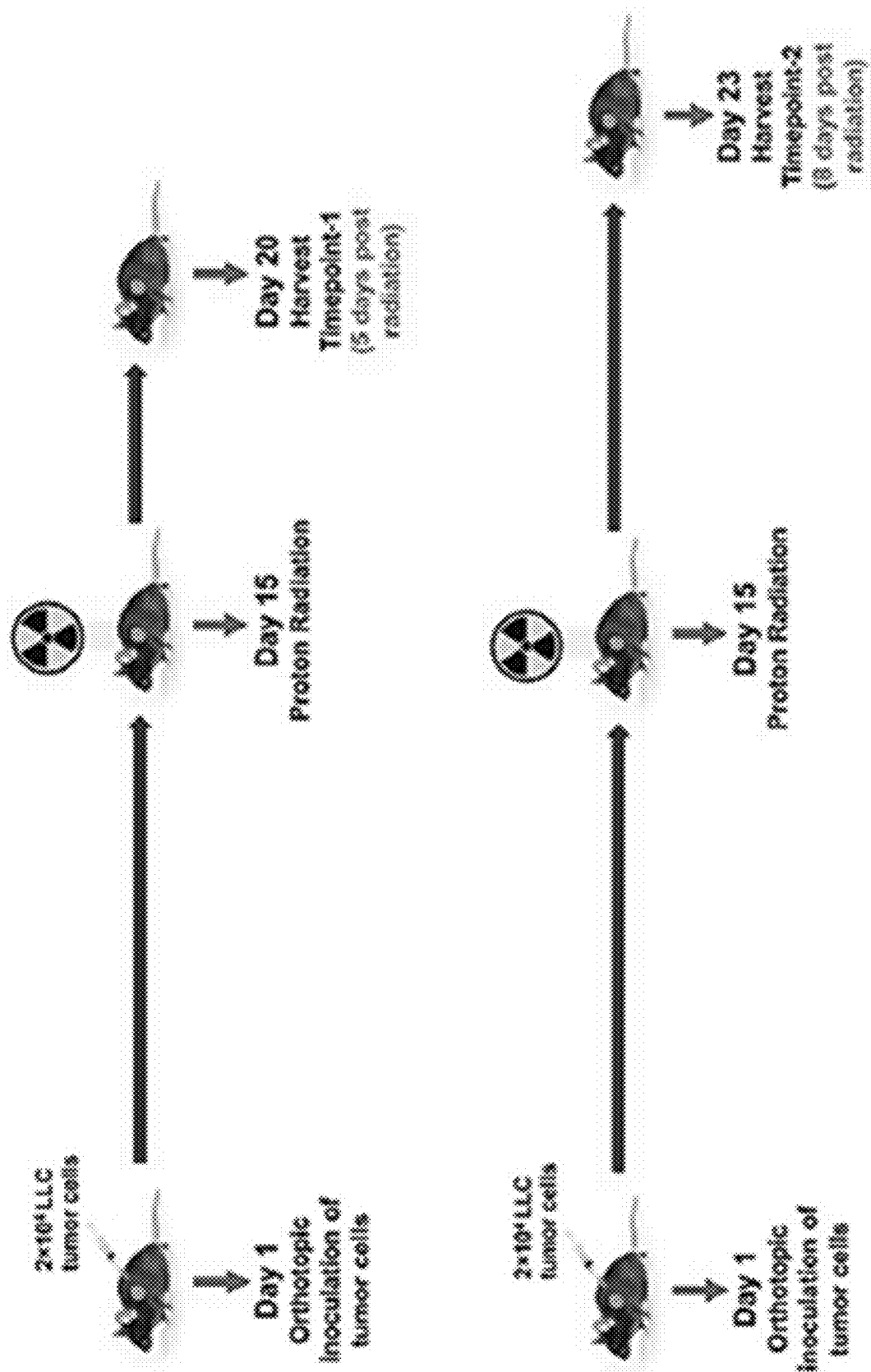
FIGS. 12A-12D.
Figure 12B:
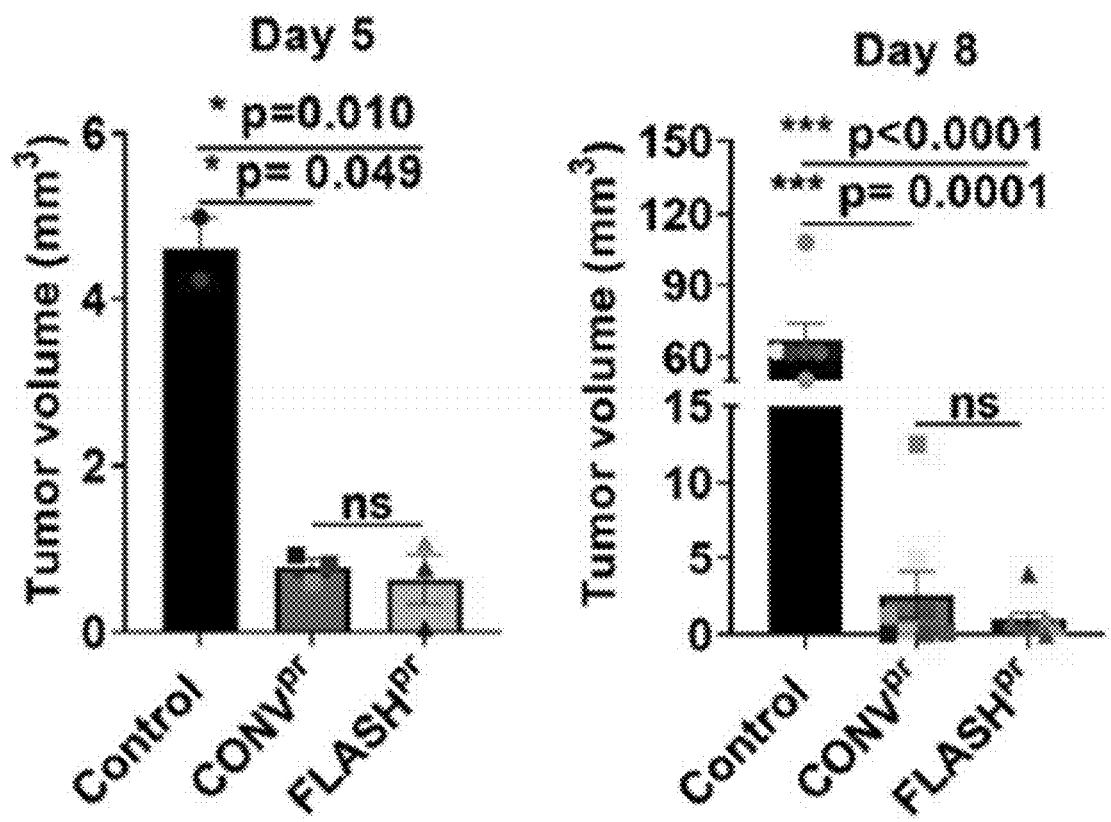
Figure 12C:
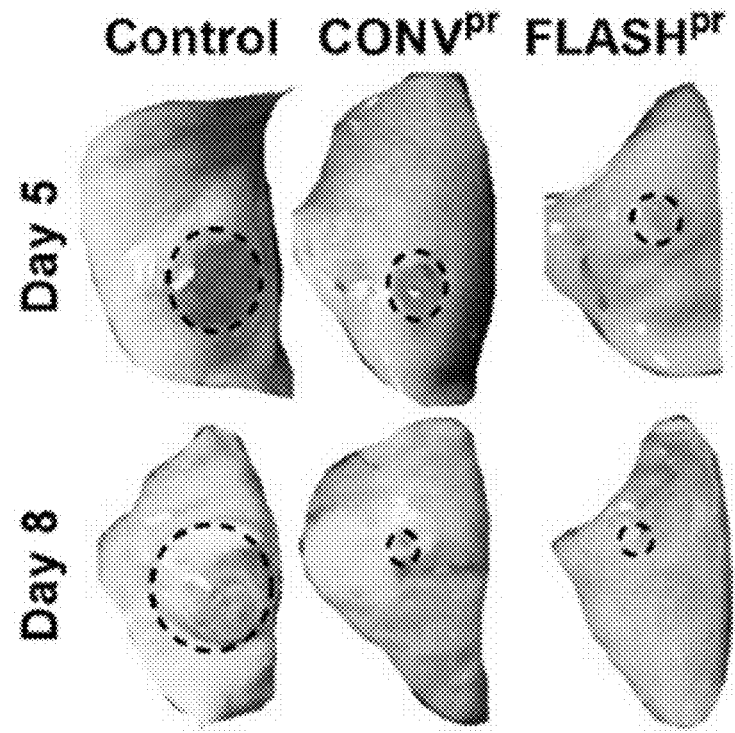
Figure 12D:
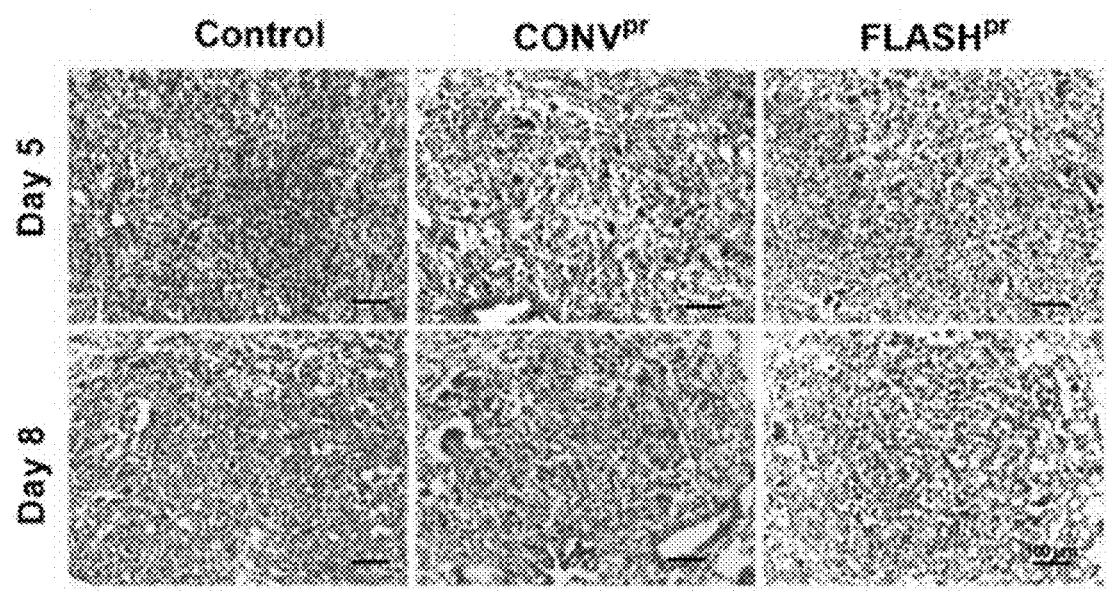

Mice treated with FLASH and CONV radiation had decreased lung tumor volumes compared to control tumor bearing mice (FIG. 12B). No significant differences were observed between the volumes of Conventional and Flash-treated tumors. Representative images of tumor-bearing left lung lobe from each group at day 5 and day 8 post radiation are shown in FIG. 12C. These data indicate that FLASH has equal efficacy in reducing lung tumor burden compared to CONV. FIG. 12D shows representative images of H&E staining of the lungs at day 5 and day 8 after treatment.

INCORPORATION BY REFERENCE

All publications, patents and patent applications references herein are incorporated by reference in their entirety.

What is claimed is:

1. A method for treating cancer in a subject, the method comprising administering to the subject no more than five fractions of proton ultra-high dose rate radiotherapy (FLASH), said fractions having a range of radiation from 1.5 Gy to 60 Gy, collectively, wherein the treatment is sufficient to prevent further growth of a tumor for at least 10% longer than standard of care radiotherapy.

2. The method of claim 1, wherein a dose of proton FLASH is equitoxic to a dose of conventional dose rate radiotherapy.

3. The method of claim 1, wherein the collective dose of radiation delivered by proton FLASH radiotherapy is contraindicated in the subject.

4. The method of claim 1, wherein the collective dose of radiation delivered by proton FLASH to the tumor is about 1.1 times, 1.2 times, 1.5 times, about 2 times, about 3 times, about 4 times, about 5 times, about 10 times or about 15 times a dose of conventional dose rate radiotherapy indicated for the cancer.

5. The method of claim 1, wherein the collective dose of radiation delivered to the tumor is about 10%, about 20%, about 30%, about 40%, about 50%, about 60%, about 70%, about 80%, about 90%, or about 100% higher than a dose of conventional dose rate radiotherapy indicated for the cancer.

6. The method of claim 1, wherein the cancer is a cancer for which radiotherapy is not indicated.

7. The method of claim 1, wherein the cancer is lung cancer, head and neck cancer, brain cancer, breast cancer or skin cancer.

8. The method of claim 1, wherein the subject is human.

9. A method for treating cancer in a subject, the method comprising administering to the subject no more than five fractions of proton ultra-high dose rate radiotherapy (FLASH), said fractions having a range of radiation from 1.5 Gy to 60 Gy, collectively, wherein the treatment is sufficient to induce at least 10% more tumor regression than standard of care radiotherapy.

10. The method of claim 9, wherein a dose of proton FLASH is equitoxic to a dose of conventional dose rate radiotherapy.

11. The method of claim 9, wherein the collective dose of radiation delivered by proton FLASH radiotherapy is contraindicated in the subject.

12. The method of claim 9, wherein the collective dose of radiation delivered by proton FLASH to the tumor is about 1.1 times, 1.2 times, 1.5 times, about 2 times, about 3 times, about 4 times, about 5 times, about 10 times or about 15 times a dose of conventional dose rate radiotherapy indicated for the cancer.

13. The method of claim 9, wherein the collective dose of radiation delivered to the tumor is about 10%, about 20%, about 30%, about 40%, about 50%, about 60%, about 70%, about 80%, about 90%, or about 100% higher than a dose of conventional dose rate radiotherapy indicated for the cancer.

14. The method of claim 9, wherein the cancer is a cancer for which radiotherapy is not indicated.

15. The method of claim 9, wherein the cancer is lung cancer, head and neck cancer, brain cancer, breast cancer or skin cancer.

16. A method for treating cancer in a subject, the method comprising administering to the subject no more than five fractions of proton ultra-high dose rate radiotherapy (FLASH), said fractions having a range of radiation from 1.5 Gy to 60 Gy, collectively, wherein the treatment results in at least 10% less, at least 20% less, at least 30% less, at least 40% less, at least 50% less, at least 60% less, at least 70% less, at least 80% less, or more than 80% less healthy tissue toxicity than standard of care radiotherapy.

17. The method of claim 16, wherein the healthy tissue toxicity is skin toxicity, muscle toxicity, or neurotoxicity.

18. The method of claim 16, wherein the collective dose of radiation delivered by proton FLASH radiotherapy is contraindicated in the subject.

19. The method of claim 16, wherein the collective dose of radiation delivered by proton FLASH to the tumor is about 1.1 times, 1.2 times, 1.5 times, about 2 times, about 3 times, about 4 times, about 5 times, about 10 times or about 15 times a dose of conventional dose rate radiotherapy indicated for the cancer.

20. The method of claim 16, wherein the collective dose of radiation delivered to the tumor is about 10%, about 20%, about 30%, about 40%, about 50%, about 60%, about 70%, about 80%, about 90%, or about 100% higher than a dose of conventional dose rate radiotherapy indicated for the cancer.

21. The method of claim 16, wherein the cancer is a cancer for which radiotherapy is not indicated.

22. The method of claim 16, wherein the cancer is lung cancer, head and neck cancer, brain cancer, breast cancer or skin cancer.

23. A method of treating brain cancer in a subject, the method comprising administering to the subject a total dose of about 10 Gy to about 60 Gy proton FLASH radiotherapy in five fractions or less at a dose rate of 40 Gy/sec or higher, wherein the cancer is brain cancer, heard and neck cancer, or breast cancer.

* * * * *